US008580286B2

(12) United States Patent
Pearlman

(10) Patent No.: US 8,580,286 B2
(45) Date of Patent: *Nov. 12, 2013

(54) COMPOSITIONS AND METHODS FOR THE TREATMENT OF SKIN DISEASES

(71) Applicant: Dale L. Pearlman, Menlo Park, CA (US)

(72) Inventor: Dale L. Pearlman, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/633,832

(22) Filed: Oct. 2, 2012

(65) Prior Publication Data

US 2013/0244987 A1    Sep. 19, 2013

Related U.S. Application Data

(63) Continuation-in-part of application No. 13/466,860, filed on May 8, 2012.

(60) Provisional application No. 61/612,203, filed on Mar. 16, 2012.

(51) Int. Cl.
*A61K 8/02* (2006.01)

(52) U.S. Cl.
USPC ........................................................ 424/401

(58) Field of Classification Search
USPC ........................................................ 424/401
See application file for complete search history.

(56) References Cited

U.S. PATENT DOCUMENTS

| | | | |
|---|---|---|---|
| 4,147,770 A | 4/1979 | Sichak | |
| 4,185,100 A * | 1/1980 | Rovee et al. | 514/171 |
| 4,246,261 A | 1/1981 | Van Scott et al. | |
| 4,954,487 A * | 9/1990 | Cooper et al. | 514/159 |
| 5,486,537 A | 1/1996 | Farinas | |
| 5,629,006 A | 5/1997 | Hoang et al. | |
| 2003/0118511 A1 | 6/2003 | Jones et al. | |
| 2008/0131385 A1 | 6/2008 | Roso et al. | |
| 2011/0070183 A1 | 3/2011 | Neumann et al. | |

OTHER PUBLICATIONS

"Guideline for Hand Hygiene in Healthcare Settings", Centers for Disease Control, [online] Oct. 25, 2002, http://www.cdc.gov/mmwr/preview/mmwrhtml/rr5116a1.htm , [retrieved Aug. 22, 2012]; pub date Oct. 25, 2002.
Acne Vulgaris, Medscape Reference Drugs, Diseases & Procedures, [online] Jun. 28, 2012, [retrieved Aug. 23, 2012] Retrieved from http://emedicine.medscape.com/article/1069804-overview ; pub date Jun. 28, 2012.
Boguniewicz M., et al.. "Atopic dermatitis: a disease of altered skin barrier and immune dysregulation." *Immunolog Rev.* 2011;24: 233-46.
Bushe L., et al. "Topical drug classification." *International Journal of Pharmaceutics* 295, 2005, 101-112.
Bunikowski R., et al. "Prevalence and role of serum IgE antibodies to the *Staphylococcus aureus*-derived superantigens SEA and SEB in children with atopic dermatitis." *J. Allergy Clin. Immunol.* 1999; 103:119-24.
Cho S-H., et.al "Fibronectin and fibrinogen contribute to the enhanced binding of *Staphylococcus aureus* to atopic skin" *J. Allergy Clin. Immunol.* 2001; 108:269-74.
Crespo-Erchiga et al., "*Malassezia* yeasts and pityriasis versicolor." *Current Opinion in Infectious Diseases* 2006, 19: (2): 139-147.
Department of Health and Human Services, Food and Drug Administration "Alcohol Drug Products for Topical Antimicrobial Over-the-Counter Human Use; Establishment of a Monograph; and Reopening of Administrative Record", Federal Register, vol. 47, No. 99, May 21, 1982.
Department of Health and Human Services, Food and Drug Administration "Topical Antimicrobial Drug Products for Over-the-Counter Human Use; Tentative Final Monograph for Healthcare Antiseptic Drug Products", Federal Register, vol. 59, No. 116, [online] Jun. 17, 1994 [retrieved Aug. 23, 2012] Retrieved from http://www.fda.gov/downloads/Drugs/DevelopmentApprovalProcess/DevelopmentResources/Over-the-counterOTCDrugs/StatusofOTCRulemakings/UCM110451.pdf ; pub date Jun. 17, 1994.
Ference and Last, "Choosing Topical Corticosteroids" *American Family Physician* 2009; 79 (2), 135-140.
Gaitanis et al., "Distribution of *Malassezia* species in pityriasis versicolor and seborrhoeic dermatitis in Greece. Typing of the major pityriasis versicolor isolate *M. globosa.*" *British Journal of Dermatology* May 2006, 154, (5), 854-859.
Hebert A.A., et al. "Safety and Efficacy of Desonide Hydrogel 0.05% in Pediatric Subjects with Atopic Dermatitis." *J Drugs Dermatol.* Feb. 2007; 6(2):175-81.
Huang J.T., et al. "Treatment of *Staphylococcus aureus* Colonization in Atopic Dermatitis Decreases Disease Severity." *Pediatrics* May 2009; 123(5): 808-814.
Kampf, et al. "Epidemiologic Background of Hand Hygiene and Evaluation of the Most Important Agents for Scrubs and Rubs" *Microbiol. Rev.*, 2004, 17(4), 863-93.
Krisanty et al., "Identification of *Malassezia* species from pityriasis versicolor in Indonesia and its relationship with clinical characteristics." *Mycoses* 2008, 52, 257-262.
Lebwohl, M., MD, "Clinical Trial: A comparison of once-daily application of mometasone furoate 0.1% cream compared with twice-daily hydrocortisone valcrate 0.2% cream in pediatric atopic dermatitis patients who failed to respond to hydrocortisone." *International Journal of Dermtology* 1999, 38, 604-606.
Leung D.Y.M., et al. "Presence of IgE Antibodies to *Staphylococcal* Exotoxins on the Skin of Patients with Atopic Dermatitis" *J. Clin. Invest.* 1993; 92:1374-80.

(Continued)

*Primary Examiner* — Benjamin Packard
(74) *Attorney, Agent, or Firm* — Wilson, Sonsini, Goodrich & Rosati

(57) ABSTRACT

Provided herein are chemical matrices, compositions, methods and devices for the treatment of skin diseases and disorders in an individual. Described herein are non-homogenous chemical matrices and compositions comprising an alcohol selected from ethanol, isopropanol or n-propanol, at least one excipient, and, optionally, at least one pharmaceutical agent, wherein the alcohol is distributed within the chemical matrix as a microbubble. Additionally, methods are described for the use of said chemical matrices and compositions for the treatment of skin diseases and disorders.

27 Claims, No Drawings

(56) References Cited

OTHER PUBLICATIONS

Miajlovic H., et al. "Effect of filaggrin breakdown products on growth of and protein expression by *Staphylococcus aureus*." *J. Allergy Clin. Immunol.* 2010; 126:1184-1190.

Morishita N., et al. "Molecular analysis of *Malassezia* microflora from patients with pityriasis versicolor." *Mycopathologia*. Feb. 2006;161(2):61-5.

Muller, R.H. et al., "Nanostructured lipid carriers (NLC) in cosmetic dermal products." *Advanced Drug Delivery Reviews* 59, 2007, (6): 522-530.

Ong P.Y ., et al. "Immune Dysregulation in Atopic Dermatitis" *Curr Allergy Asthma Rep.* Sep. 2006; 6(5):384-9.

Pagnoni A., et al. "Lack of burning and stinging from a novel first-aid formulation applied to experimental wounds." *J. Cosmet. Sci.* Mar.-Apr. 2004; 55(2):157-62.

PCT/US2012/36966 International Search Report and Written Opinion dated Jul. 30, 2012.

Psoriasis, Medscape Reference Drugs, Diseases & Procedures, [online] Aug. 6, 2012, [retrieved Aug. 23, 2012] Retrieved from http://emedicine.medscape.com/article/1943419-overview#a0156 ; pub date Aug. 6, 2012.

Rafanelli A., et al. "Mometasone furoate in the treatment of atopic dermatitis in children." *J. Eur. Acad. Dermatol. Venereol.* 1993; 2(3):225-230.

Reginald K., et.al. "*Staphylococcus aureus* fibronectin-binding protein specifically binds IgE from patients with atopic dermatitis and requires antigen presentation for cellular immune responses." *J. Allergy Clin. Immunol.* 2011; 128:82-91.

Rincon et al., "*Malassezia* yeast species isolated from patients with dermatologic lesions." Biomedica 2005; 25: 189-195.

Rosacca Incidence on Rise, National Rosacea Society, [online] Apr. 1, 2010, [retrieved Aug. 23, 2012] Retrieved from http://www.rosacea.org/weblog/2010/04/01/rosacea_incidence_on_rise/index.php , pub date Apr. 1, 2010.

Tinea Pedis, Medscape Reference Drugs, Diseases & Procedures, [online] Jan. 24, 2012, [retrieved Oct. 2, 2012] Retrieved from http://emedicine.medscape.com/article/1091684-overview#a0199, pub date Jan. 24, 2012.

Trookman, N.S., et al. "Randomized Controlled Trial of Desonide Hydrogel 0.05% versus Desonide Ointment 0.05% in the treatment of Mild-to-Moderate Atopic Dermatitis." *J. Clin Aesthet Dermatol.* Nov. 2011; 4(11): 34-38.

Trookman, N.S., et al. "Irritation and allergy patch test analysis of topical treatments commonly used in wound care: Evaluation on normal and compromised skin." *J. Amer. Acad. Dermatol.* Mar. 2011; 64(3), Suppl 1:S16-22.

US Food and Drug Administration, Drug Nomenclature Monograph, No. C-DRG-00201 [online] Jan. 30, 2009, [retrieved online Aug. 22, 2013] Retrieved from http://www.fda.gov/Drugs/DevelopmentApprovalProcess/FormsSubmissionRequirements/ElectronicSubmissions/DataSatndardsManualmonographs/ucm071666.htm; pub date Jan. 30, 2009.

Vernon H.J., et al. "Comparison of mometasone furoate 0.1% cream and hydrocortisone 1.0% cream in the treatment of childhood atopic dermatitis." *J. Am. Acad. Dermatol.* Apr. 1991; 24:603-7.

Zollner TM et al. "Colonization with superantigen-producing *Staphylococcus aureus* is associated with increased severity of atopic dermatitis." *Clin. Exp. Allergy* 2000; 30: 994-1000.

* cited by examiner

COMPOSITIONS AND METHODS FOR THE TREATMENT OF SKIN DISEASES

CROSS REFERENCE

This application claims the benefit of U.S. Provisional Application No. 61/612,203, filed Mar. 16, 2012, and U.S. application Ser. No. 13/466,860, filed May 8, 2012, the contents of which are hereby incorporated by reference in their entireties.

BACKGROUND OF THE INVENTION

High ethanol content sanitizer gel is known to be a very effective topical antimicrobial agent for preventing infections. Direct application to bacterial, fungal, and viral organisms in the laboratory setting results in 99.99% killing within 15 seconds of contact. This efficacy is due to its concentration of ethyl alcohol greater than, or equal to, 60% (Federal Register, Vol. 59, No. 116, Jun. 17, 1994). Similar antiseptic activity has been observed for isopropanol (Federal Register, Vol. 47, No. 99, May 21, 1982). In current commercial formulations, the ethanol containing gel typically contains special moisturizers to control dryness on users' hands so they tolerate such a high concentration of ethyl alcohol. However, use of these gels containing greater than, or equal to, 60% ethyl alcohol on skin damaged with cracks, tears and/or fissures results in a pronounced stinging sensation (Guideline for Hand Hygiene in Health-care Settings, Centers for Disease Control, http://www.cdc.gov/mmwr/preview/mmwrhtml/rr5116a1.htm).

SUMMARY OF THE INVENTION

One embodiment disclosed herein provides a means of applying ethanol to the skin without stinging.

One embodiment provides a chemical matrix comprising from about 2% to about 30% of an alcohol by volume, a corticosteroid and at least one excipient, wherein the chemical matrix is an ointment suitable for topical administration, the alcohol is primarily dispersed into the chemical matrix in the form of microbubbles, and the alcohol is selected from ethanol, isopropanol, or n-propanol.

Another embodiment provides the chemical matrix wherein the alcohol is ethanol. Another embodiment provides the chemical matrix wherein the chemical matrix comprises from about 2% to about 10% ethanol by volume. Another embodiment provides the chemical matrix wherein the chemical matrix comprises from about 10% to about 20% ethanol by volume. Another embodiment provides the chemical matrix wherein the chemical matrix comprises from about 20% to about 30% ethanol by volume.

Another embodiment provides the chemical matrix wherein the ointment is selected from aquaphore, white petrolatum USP, white ointment USP, hydrophilic petrolatum USP, or hydrophilic ointment USP.

Another embodiment provides the chemical matrix wherein the corticosteroid is selected from desonide, or mometasone. Another embodiment provides the chemical matrix wherein the corticosteroid comprises from about 0.1% (w/w) to about 0.0001% (w/w) of the chemical matrix. Another embodiment provides the chemical matrix wherein the chemical matrix comprises from about 2% to about 10% ethanol by volume and the corticosteroid is selected from desonide, or mometasone. Another embodiment provides the chemical matrix wherein the chemical matrix comprises from about 10% to about 20% ethanol by volume and the corticosteroid is selected from desonide, or mometasone. Another embodiment provides the chemical matrix wherein the chemical matrix comprises from about 20% to about 30% ethanol by volume and the corticosteroid is selected from desonide, or mometasone.

Another embodiment provides the chemical matrix wherein the chemical matrix comprises from about 2% to about 10% ethanol by volume, the corticosteroid is selected from desonide, or mometasone, and the corticosteroid comprises from about 0.1% (w/w) to about 0.0001% (w/w) of the chemical matrix. Another embodiment provides the chemical matrix wherein the chemical matrix comprises from about 10% to about 20% ethanol by volume, the corticosteroid is selected from desonide, or mometasone, and the corticosteroid comprises from about 0.1% (w/w) to about 0.0001% (w/w) of the chemical matrix. Another embodiment provides the chemical matrix wherein the chemical matrix comprises from about 20% to about 30% ethanol by volume, the corticosteroid is selected from desonide, or mometasone, and the corticosteroid comprises from about 0.1% (w/w) to about 0.0001% (w/w) of the chemical matrix.

One embodiment provides a method of treating a skin disease or disorder in an individual in need thereof comprising topical application to the individual of a chemical matrix comprising from about 2% to about 30% of an alcohol by volume, a corticosteroid and at least one excipient, wherein the chemical matrix is an ointment suitable for topical administration, the alcohol is primarily dispersed into the chemical matrix in the form of microbubbles, and the alcohol is selected from ethanol, isopropanol, or n-propanol.

Another embodiment provides the method wherein the alcohol is ethanol. Another embodiment provides the method wherein the chemical matrix comprises from about 2% to about 10% ethanol by volume. Another embodiment provides the method wherein the chemical matrix comprises from about 10% to about 20% ethanol by volume. Another embodiment provides the method wherein the chemical matrix comprises from about 20% to about 30% ethanol by volume. Another embodiment provides the method wherein the ointment is selected from aquaphore, white petrolatum USP, white ointment USP, hydrophilic petrolatum USP, or hydrophilic ointment USP. Another embodiment provides the method wherein the corticosteroid is selected from desonide, or mometasone. Another embodiment provides the method wherein the corticosteroid comprises from about 0.1% (w/w) to about 0.0001% (w/w) of the chemical matrix. Another embodiment provides the method wherein the chemical matrix comprises from about 2% to about 10% ethanol by volume and the corticosteroid is selected from desonide, or mometasone. Another embodiment provides the method wherein the chemical matrix comprises from about 10% to about 20% ethanol by volume and the corticosteroid is selected from desonide, or mometasone. Another embodiment provides the method wherein the chemical matrix comprises from about 20% to about 30% ethanol by volume and the corticosteroid is selected from desonide, or mometasone.

Another embodiment provides the method wherein the chemical matrix comprises from about 2% to about 10% ethanol by volume, the corticosteroid is selected from desonide, or mometasone, and the corticosteroid comprises from about 0.1% (w/w) to about 0.0001% (w/w) of the chemical matrix. Another embodiment provides the method wherein the chemical matrix comprises from about 10% to about 20% ethanol by volume, the corticosteroid is selected from desonide, or mometasone, and the corticosteroid comprises from about 0.1% (w/w) to about 0.0001% (w/w) of the chemical matrix. Another embodiment provides the method wherein the chemical matrix comprises from about 20% to about 30% ethanol by volume, the corticosteroid is selected from desonide, or mometasone, and the corticosteroid comprises from about 0.1% (w/w) to about 0.0001% (w/w) of the chemical matrix.

Another embodiment provides the method wherein the skin disease or disorder is dermatitis. Another embodiment provides the method wherein the skin disease or disorder is eczema. Another embodiment provides the method wherein the skin disease or disorder is atopic dermatitis.

DETAILED DESCRIPTION OF THE INVENTION

New treatments are needed for many dermatologic diseases because current treatments lack efficacy, exhibit side effects, or are so unpleasant to use that patients are discouraged from using them. In a series of clinical trials it has been found that, in comparison to current treatments, use of the compositions described herein produces clinical outcomes characterized by equal or higher efficacy, while exhibiting minimal side effects and good patient compliance.

It has been discovered that certain topical compositions (lotions, creams, ointments, emulsions and dispersions) that contain ethanol or certain other alcohols distributed non-homogenously have the unexpected benefit of effectively treating a variety of dermatologic diseases and disorders. Whereas previously known only for maintaining hygiene on healthy skin, now it is possible to use topical compositions containing ethanol or certain other alcohols to treat diseases and disorders of the skin wherein the skin is damaged, broken, torn, or marked by fissures. These skin diseases and disorders range from infections (bacterial or fungal) to inflammatory diseases (dermatitis, psoriasis, acne vulgaris, or rosacea). It has been also discovered that the topical compositions described herein can be safely used on the face. Effective treatments can be achieved, in some cases, through use of the topical compositions described herein wherein ethanol or another alcohol is the sole active ingredient. Further advantages can be obtained by incorporating into said compositions at least one additional therapeutic active agent. One distinguishing feature of these compositions is the non-homogenous nature of the formulation. In particular, it has been found that when the ethanol or other alcohol is distributed in a non-homogenous fashion throughout the composition into bubble-like regions of locally high concentration, where the approximate effective concentration of the ethanol or other alcohol in the bubble-like regions is about 60% to about 80%, a beneficial effect is observed upon topical application to damaged skin but without a stinging sensation. This result is striking when compared to the well-known stinging sensation observed upon application of commercially available high ethanol content sanitizers gels to damaged skin.

DEFINITIONS

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "noncomedogenic" describes the tendency of some dermatological products, such as oils, lotions, ointments, creams, and gels to block the pores of the skin. Noncomedogenic products are less likely to clog pores and lead to formation of blackheads (open comedones), whiteheads (closed comedones), red bumps (inflammatory papules) and red, swollen, pussy red bumps and lumps (inflammatory pustules, nodules, and cysts) in patients' skin. Comedogenic ingredients of many commercially available skin care products include isopropyl myristate, cocoa butter, coconut oils, and wheat germ oil.

The term "subjective irritation" describes burning, stinging, or itching without detectable visible or microscopic changes in the skin.

The term "non-homogeneous" describes the lack of a uniform phase throughout the bulk, or entirety, of the composition. The terms "non-homogeneous" and "heterogeneous" are synonymous and can be used interchangeably. As used herein, the terms "non-homogeneous" and "heterogeneous" refer to the bulk, or entirety, of the composition as employed by the patient or caregiver.

The term "semisolid" describes a material that has the properties of a solid and of a liquid.

The term "gel" describes a semisolid dosage form that contains a gelling agent to provide stiffness to a solution or colloidal dispersion (US FDA Drug Nomenclature Monograph, number C-DRG-00201). A gel may contain suspended particles. A gel can contain >50% water and other volatiles (Buhse L, et. al. International Journal of Pharmaceutics; 295: 101-112). A gel offers nongreasy medication delivery.

The term "oil" describes an unctuous, combustible substance which is liquid, or easily liquefiable, on warming, and is soluble in ether but insoluble in water. Oils are classified as animal, mineral or vegetable oils, depending on their origin (US FDA Drug Nomenclature Monograph, number C-DRG-00201).

The term "emulsion" describes a dosage form consisting of a two-phase system comprised of at least two immiscible liquids, one of which is dispersed as droplets (internal or dispersed phase) within the other liquid (external or continuous phase) generally stabilized with one or more emulsifying agents (US FDA Drug Nomenclature Monograph, number C-DRG-00201).

The term "lotion" describes an emulsion liquid dosage form. This dosage form is generally for external application to the skin (US FDA Drug Nomenclature Monograph, number C-DRG-00201). A lotion may contain moisturizing agents which can help increase skin moisture. A lotion may contain small amounts of alcoholic preservatives to prevent microbial growth during product life.

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin or mucous membranes (US FDA Drug Nomenclature Monograph, number C-DRG-00201). A cream may contain moisturizing agents which can help increase skin moisture. A cream may contain alcoholic preservatives to prevent microbial growth during product life.

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201). An ointment offers a dense, occlusive covering which increases hydration of dry skin rashes.

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "high ethanol content" describes a composition comprising throughout the bulk or entirety of the composition, greater than or equal to 60% ethyl alcohol content. Commercially available hand sanitizer gels are one example of a high ethanol content composition (Federal Register, Vol. 59, No. 116, Jun. 17, 1994).

Skin Diseases and Disorders
Acne Vulgaris ("Teenage Acne")

Acne is a common skin disease that affects 60-70% of Americans at some time during their lives (http://emedicine.medscape.com/article/1069804-overview). Teenagers may need ongoing treatment from age 12 to 23 years old.

Acne vulgaris is characterized by the onset around puberty of comedones and inflammatory lesions on the face, neck, chest, and back. It tends to resolve on average around age 23 years of age. The pathogenesis is multifactorial. There is increased oil production by increasingly active skin oil glands under the influence of puberty associated hormones. An obstruction of the secretory tubules ("pores") which connect the gland to the skin surface leads to accumulation of oil under the skin surface. As the volume increases the lumps called comedones become visible. Bacteria then proliferate in the oil leading to further inflammation in the skin causing the formation of the visible red papules, pustules, nodules, and cysts typically seen in acne vulgaris. The specific bacteria infecting these lesions has been identified as *Proprionobacterium acnes*. These lesions can be uncomfortable or tender, can create disfigurement of the teenager compared to his peers, leading to embarrassment in affected boys and girls. Thus teenagers frequently seek treatment to minimize this disorder.

Treatment is based on agents which seek to correct the fundamental pathologic events creating acne lesions.

Topical treatments fall into several classes:

a) "Comedolytic agents" dissolve the secretory tubule obstruction thus allowing drainage of the trapped oil. Topical agents of this type include: sulfur, resorcinol, salicyclic acid, glycolic acid, retinoids such as tretinoin, adapaline and tazarotene, and benzoyl peroxide.

b) "Antibacterial agents" suppress the bacterial population. Topical agents of this class include: benzoyl peroxide, antibiotics (erythromycin, clindamycin), and astringents, and nonspecific mechanism agents like azelaic acid.

c) "Cleansers" seek to dissolve surface oil, dissolve clogged pores, and remove bacteria. Oral treatments: These include oral antibiotics (tetracycline family, erythromycin macrolide family, ampicillin penicillin family) which suppress the bacteria. The oral agent 13-cis-retinoic acid (Accutane™) seeks to reduce oil production and resolve clogging of the pores.

In some embodiments, the compositions and methods described herein are useful for the treatment of acne vulgaris. In some embodiments, the compositions and methods described herein are an excellent first line treatment for mild to moderate, and some cases, severe pustular acne seen in teenagers. The compositions and methods described herein can be used independently, or in combination with over-the-counter and/or prescription dispensed therapeutically active agents to address all types of acne lesions. In some embodiments, the compositions disclosed herein include at least one comedolytic agent. In some embodiments, the compositions disclosed herein include at least one anti-inflammatory agent. In some embodiments, the compositions disclosed herein include at least one antibiotic agent.

Rosacea ("Adult Acne")

In this disorder, adults, usually 25 years and older, develop a triad of distinctive features separating it from acne vulgaris ("teenage acne"). The triad consists of:

a) central facial increased redness and increased surface blood vessels;

b) central facial inflammatory red papules, pustules, and nodules;

c) tendency to easy facial flushing and blushing in response to trigger factors including certain psychological states (embarrassment or anger), exercise during workouts, consumption of alcoholic drinks and hot coffee/tea.

The condition can last for many years and gradually worsen. Patients are usually motivated to seek treatment because of the disfigurement of the skin disorder.

In a recent study, Dr. Maeve McAleer and colleagues at the School of Public Health and Population Science, University College, Dublin, found that 14.4 percent of 1,000 subjects examined in Ireland had rosacea. Moreover, in a 1989 study of 800 office workers in Sweden, the prevalence of rosacea was 10 percent—including 14 percent in women and 6 percent in men (http://www.rosacea.org/weblog/2010/04/01/rosacea_incidence_on_rise/index.php).

The specific pathogenesis of rosacea is not known. The same bacteria found infecting acne vulgaris lesions has not been found in rosacea. There are no plugged up pores (comedones) present in rosacea patients. There are many hypotheses for rosacea causation revolving around a postulated bacteria which infects the skin leading to the inflammation so characteristic of the condition.

Treatment of rosacea involves the use of topical and oral agents.

Topical Agents:

a) Antimicrobial agents: metronidazole, sulfa/sulfur combinations, clindamycin, benzoyl peroxide;

b) Anti-inflammatory agents of uncertain mechanism: azelaic acid.

Oral Agents:

a) Antibacterial agents: These include oral antibiotics (tetracycline family, erythromycin macrolide family, ampicillin penicillin family) which suppress growth of bacteria and/or kill bacteria.

Use of the compositions and methods described herein is a very effective topical treatment for red bumps and pussy bumps of rosacea. The treatment produces clinical improvement noticeable to the patients within a week of starting treatment. Of equal significance is that this treatment rapidly reduces central facial redness. This is not true of topical Finacea™ or Metrogel™ which are the current standard of care for this indication. Advantages of the compositions and methods disclosed herein for the treatment of rosacea over current topical treatments, such as Finacea and Metrogel, include faster onset of relief, reliably reduces redness, no stinging, less costly, and reduced environmental impact. Advantages of the compositions and methods disclosed herein for the treatment of rosacea over current oral include no concerns about safety of oral antibiotics, no upset stomach or sun sensitization issues, no impact on use of oral contraceptives, no issue of vaginal yeast infections, and reduced environmental impact. In some embodiments, the compositions and methods described herein are useful for the treatment of rosacea. In some embodiments the compositions disclosed herein include at least one anti-inflammatory agent. In some embodiments, the compositions disclosed herein include at least one antibiotic agent.

Dermatitis

Dermatitis, or eczema, is a common, very uncomfortable, frequently very itchy, rash characterized by red, scaly, patches in the skin. The redness, swelling, and discharge are all signs of inflammation of an allergic type process. The classification of the dermatitis is determined by the appearance and distribution of the patches and the demographics of the patient. For example, atopic dermatitis is characterized by rash patches located typically in the fronts of the elbows and behind the knees in young children. Nummular dermatitis is characterized by round rash patches scattered randomly on the trunk and limbs of adults. Contact dermatitis is characterized by linear shaped swollen patches on the trunk or limbs at any age.

Prior to the discovery of the methods, compositions and devices disclosed herein, the use of high ethanol content gels in the treatment of eczema was complicated by a stinging sensation upon topical application. This stinging occurs because the acute phase of the rash is characterized by many small cracks and fissures in the skin. By using the methods, compositions and devices disclosed herein to treat the acute phase of eczematous lesions topical application of the composition does not cause a stinging sensation. Maintenance therapy employing the methods, compositions and devices disclosed herein to suppress the recurrence of eczematous lesions is provided by application of the composition, such that topical application of the composition does not cause a stinging sensation.

During the sub-acute phase (rash but no fissures) the composition disclosed herein is well tolerated and can greatly increase efficacy of concomitant or subsequent topical steroid therapy in resolving the remaining rash. Once the eczema is resolved, ongoing use of the compositions as disclosed herein that do not contain corticosteroid can help sustain the disease-free remission period. The addition of moisturizing ingredients to the compositions disclosed herein can keep the skin moist.

In some embodiments, the compositions and methods described herein are useful for the treatment of dermatitis. In some embodiments the compositions disclosed herein include at least one anti-inflammatory agent.

Atopic Dermatitis

Atopic dermatitis occurs in approximately 10-20% of children and 2% of adults (Ong P Y, Leung D Y. Immune dysregulation in atopic dermatitis. *Curr Allergy Asthma Rep.* September 2006; 6(5):384-9).

In the developed countries of North America and Europe, children from ages 2 to 8 years commonly suffer from this itching, unattractive rash. The discomfort and sleep deprivation are a major burden for patients and their families.

Treatment of eczema is difficult and often requires a multi-faceted approach. Moisturizers are administered to relieve dry skin. Cold compresses can relieve itch. Corticosteroid and topical calcineurin inhibitors can reduce inflammation. Antibiotics treat bacterial infection. Sedative antihistamines can enable sleep and rest. For moderate to severe cases, phototherapy can be used.

The latest scientific understanding of the causes of eczema highlight the unmet medical need satisfied by the methods, compositions and devices disclosed herein. In patients with eczema, the skin is drier than usual with outer layer cracks and fissures which facilitate easy colonization by a particular bacterium, *Staphylococcus aureus* (Boguniewicz M, Leung D Y M. Atopic dermatitis: a disease of altered skin barrier and immune dysregulation. *Immunolog Rev.* 2011; 24:233-46). The staphylococcal population density in the skin rises greatly because the patients are deficient in some of the usual factors required to defend against them (Miajlovic H, Fallon P G, Irvine A D, Foster T J. Effect of filaggrin breakdown products on growth of and protein expression by *Staphylococcus aureus*. *J. Allergy Clin. Immunol.* 2010; 126:1184-1190; Cho S-H, Strickland I, Boguniewicz M, et. al. Fibronectin and fibrinogen contributes to the enhanced binding of *S. aureus* to atopic skin. *J. Allergy Clin. Immunol.* 2001; 108:269-74; Bunikowski R, Mielke M, Skarabis H, et al. Prevalence and role of serum IgE antibodies to the Staphylococcus aureus-derived superantigens SEA and SEB in children with atopic dermatitis. *J. Allergy Clin. Immunol.* 1999; 103:119-24; Leung D Y M, Harbeck R, Bina P, et al. Presence of IgE antibodies to staphylococcal exotoxins on the skin of patients with atopic dermatitis: evidence for a new group of allergens. *J. Clin. Invest.* 1993; 92:1374-80; Zollner T M, Wichelhaus T A, Hartung A, et al. Colonization with super-antigen-producing Staphylococcus aureus is associated with increased severity of atopic dermatitis. *Clin. Exp. Allergy* 2000; 30: 994-1000). The staphylococci worsen the eczema by an immune mechanism which up-regulates inflammation culminating in the symptoms and appearance of the visible eczema rash (Reginald K, Westritschnig K, Linhard B, Focke-Tejkl M, et. al. *Staphylococcus aureus* fibronectin-binding protein specifically binds IgE from patients with atopic dermatitis and requires antigen presentation for cellular immune responses. *J. Allergy Clin. Immunol.* 2011; 128: 82-91).

Measures which decrease this bacterial population are generally found to help resolve eczema. Oral and topical antibiotics currently are used for this purpose. Previously, high ethanol content gels were to be avoided due to the stinging sensation upon topical application as the stinging sensation would lead to a lack of patient compliance.

While the use of "bleach baths" has recently been shown to improve eczema by lowering the *S. aureus* skin population (Huang J T, Abrams M, Tlougan B, Rademaker A, Paller A S. Treatment of staphylococcus aureus colonization in atopic dermatitis decreases disease severity. *Pediatrics* May 2009; 123(5): 808-814) caregivers are reluctant to use this treatment because of the time and effort required. This effort includes preparing the bath, cleaning up afterwards, ventilating the bathroom to remove the bleach odor, and trying to avoid bleaching bathroom linens.

Use of the compositions as described herein is a significant advance for topical therapy in eczema. Caregivers find applying the compositions described herein to be an easy and familiar way of treating skin problems. The caregiver applies a single composition that contains a secondary topical medication. This single composition is formulated to cause no irritation to the skin, such as a stinging sensation. Preferred dosage forms of this composition include non-homogenous ointments, lotions, creams and other emulsions or dispersions where the ethanol can be suspended or dispersed in the non-aqueous component to avoid a stinging sensation upon topical application. In some embodiments, the compositions and methods described herein are useful for the treatment of atopic dermatitis. In some embodiments the compositions disclosed herein include at least one anti-inflammatory agent. In some embodiments the compositions disclosed herein include at least one corticosteroid.

Contact Dermatitis

Irritant contact dermatitis can occur after brief exposure to a strong irritant or frequent exposure to a mild irritant. When contact with the irritant damages the skin faster than the skin can repair itself, irritant contact dermatitis can develop.

Allergic contact dermatitis usually develops within hours after the allergen makes skin contact. Nearly 3000 allergens are known to cause allergic contact dermatitis. Common allergens include fragrances, metals, plants, clothing and shoes.

Current treatments include avoidance of the irritant or allergen, frequent use of topical moisturizers, application of topical corticosteroid to reduce inflammation and administration of antibiotics should an infection develop. Phototherapy can be used in severe cases to suppress the overactive immune response.

In some embodiments, the compositions and methods described herein are useful for the treatment of contact dermatitis.

Dyshidrotic Dermatitis (Hand Eczema)

Dyshidrotic dermatitis, also known as hand eczema, pompholyx, vesicular eczema, or vesicular palmoplantar eczema, occurs only on the palms of the hands, sides of fingers and soles of the feet. It typically causes a burning, itching sensation and a blistering rash.

Patients with dyshidrotic dermatitis are typically between 20 and 40 years of age. Risk factors include stress and pre-existing conditions (atopic condition, contact dermatitis, infection).

Current treatments include the use of topical corticosteroid and cold compresses, antibiotics, topical medications to relieve pain and itch, and topical calcineurin inhibitors to reduce inflammation as well as drainage of large blisters to relieve pain.

In some embodiments, the compositions and methods described herein are useful for the treatment of dyshidrotic dermatitis.

Seborrheic Dermatitis (Seborrheic Eczema)

Seborrheic dermatitis, also known as cradle cap, seborrhea, or dandruff, usually begins on the scalp as oily, waxy patches and can sometimes spread to the face and beyond. Symptoms can also include flaking skin; reddish, somewhat swollen skin; and constant itchiness. In some cases, seborrheic dermatitis is thought to be triggered by the microorganism malassezia.

Current treatments include administration of a topical mild corticosteroid and topical anti-fungal medication, such as ketoconazole, as well as the use of a specific shampoo regimen.

In some embodiments, the compositions and methods described herein are useful for the treatment of seborrheic dermatitis.

Nummular Dermatitis (Eczema)

Nummular dermatitis presents itself as unique, coin-shaped or oval lesions.

Approximately 2 out of every 1000 people in the United States develop nummular eczema. Men develop it more frequently, with the first incident occurring between 55 and 65 years of age. Women tend to develop nummular dermatitis between 15 and 25 years of age.

Current treatments include methods to hydrate the skin (use of a humidifier, use of moisturizers) and the use of topical and/or oral medications (corticosteroids, antibiotics, antihistamine).

In some embodiments, the compositions and methods described herein are useful for the treatment of nummular dermatitis.

Neurodermatitis (Eczema)

Neurodermatitis develops when nerve endings in the skin become irritated, triggering a severe itch-scratch-itch cycle. Common causes of nerve irritation include an insect bite and emotional stress.

Neurodermatitis occurs more frequently in people who have psoriasis or contact dermatitis, people who have an atopic condition (atopic dermatitis, hayfever, asthma), females, and people between 30 and 50 years of age.

Current treatments include administration of a topical corticosteroid, a topical or oral antibiotic, a topical keratolytic, and a sedative/tranquilizer.

In some embodiments, the compositions and methods described herein are useful for the treatment of neurodermatitis.

Stasis Dermatitis (Eczema)

Stasis dermatitis, also known as gravitational dermatitis, venous dermatitis, or venous stasis dermatitis, develops in the lower legs when circulation becomes sluggish. Poor blood flow leads to fluid build-up. The legs swell, causing the development of a rash that usually itches, painful sores and discolored thinning skin.

In the United States, about 15-20 million people over 50 years of age have stasis dermatitis.

Current treatments include methods to increase blood flow in the legs as well as the administration of topical and/or oral medications (corticosteroids, antibiotics).

In some embodiments, the compositions and methods described herein are useful for the treatment of stasis dermatitis.

Hand Dermatitis (Eczema)

Hand dermatitis is not one specific type of eczema but rather any type of eczema that develops on the hands.

Estimates indicate that between 2% and 10% of Americans have some form of hand dermatitis. Hand dermatitis may account for 80% of all job-related skin conditions. People in occupations that involve frequent hand immersion in water are more susceptible to the development of hand dermatitis.

Current treatments include administration of topical or oral corticosteroids and/or antibiotics, topical tars, and topical calcineurin inhibitors as well as the use of phototherapy or botulinum toxin type A injections.

In some embodiments, the compositions and methods described herein are useful for the treatment of hand dermatitis.

Occupational Dermatitis (Eczema)

Occupational dermatitis is not one specific type of eczema but rather any type of eczema that is caused by a person's workplace.

Estimates indicate that 5% of men and 10% of women in the workforce develop eczema on their hands from workplace exposure. Often, the eczema is the result of an irritant (irritant contact dermatitis) or an allergic reaction (allergic contact dermatitis). Occupational dermatitis can also occur on the face and forearms.

Current treatments include avoidance of the irritant/allergen, frequent use of topical moisturizers, application of topical corticosteroid to reduce inflammation and administration of antibiotics should an infection develop. Phototherapy can be used in severe cases to suppress the overactive immune response.

In some embodiments, the compositions and methods described herein are useful for the treatment of occupational dermatitis.

Secondarily Infected Dermatitis

Due to the marked itchiness of rashes, dermatitis patients frequently scratch the affected skin disrupting its integrity and providing a "portal of entry" for bacteria to infect the skin. Thus a rash which began with only inflammation soon becomes so called "secondarily" infected with bacteria. This colonization of the rash with an overgrowth of abnormal bacteria (often Staphylococcus aureus) further contributes to skin irritation. Thus, because a secondary infection has occurred, effective treatment of the rash must suppress both inflammation and infection.

Treatment of dermatitis employs several classes of therapeutic agents.

Topical Treatment:

a) Immunosuppressive agents to reduce inflammation include corticosteroids such as hydrocortisone and many other related molecules, and immunomodulating agents such as tacrolimus and pimecrolimus.

b) Antibacterial agents to suppress bacterial infection include mupirocin, retapamulin, neomycin, bacitractin, polymyxin, and sulfa.

Oral Treatment:

a) Immunosuppressive agents to reduce inflammation include corticosteroids like prednisone b) Antibiotics to suppress bacterial infection include tetracycline family, erythromycin macrolide family, penicillin family, cephalosporin family, ciprofloxacin family, and clindamycin.

c) oral antihistamines to reduce the itch and swelling of inflammation.

Use of compositions as described herein dramatically improves the efficacy of topical steroids while eliminating the need for topical and oral antibiotics. This simpler treatment means better compliance and better success in treatment.

In some embodiments, the compositions and methods described herein are useful for the treatment of secondarily infected dermatitis. In some embodiments, the compositions disclosed herein include at least one immunosuppressive agent. In some embodiments, the compositions disclosed herein include at least one antimicrobial agent.

Pitted Keratolysis

Pitted keratolysis is a distinctive non-inflammatory bacterial infection of the soles of the feet that is characterized by appearance of pits on the soles. It usually occurs in teenagers and young adults with sweat soaked skin due to athletic activities and not changing to dry socks. This wet condition leads to maceration and breakdown of the outer skin layer creating a portal of entry for a specific bacteria: *Erythromyces minitussitum*. It is foul smelling and gives a "swiss cheese" appearance to the soles of the feet.

Current standard of treatment includes topical application of agents to decrease sweating to dry the feet (aluminum chloride) and antibacterial agents to suppress the bacterial infection (erythromycin, or clindamycin).

In some embodiments, the compositions and methods described herein are useful for the treatment of pitted keratolysis.

Athlete's Foot (Tinea Pedis)

Tinea pedis is thought to be the world's most common dermatophytosis. Reportedly, 70% of the population will be infected with tinea pedis at some time (http://emedicine.medscape.com/article/1091684-overview#a0199).

In this fungal infection of the soles, there are dry pink to tan scaly patches which gradually expand to cover the sole and the web spaces between the toes. Often cracks occur due to the dryness causing decreased skin flexibility. Symptoms often range from mild to severe itching from the inflammation of the skin and mild to severe discomfort due to the cracks. Typically it begins in teen years and can last through adulthood. Sometimes painful blisters can occur due to the intense inflammation induced by the immune defense response to the fungal infection.

Current standard of treatment includes administration of topical agents and/or the use of oral agents. Topical treatment include antifungal agents such as terbenafine, econazole, miconazole, clotrimazole, butenafine, tolnaftate, or salicylic acid. All of these agents typically take 2-4 weeks to improve the rash. Oral agents used for the treatment of tinea pedis include griseofulvin, terbenafine, itraconazole, or fluconazole. While effective, these pose risks of toxicity including blood, liver, and heart injury.

In some embodiments, the compositions and methods described herein are useful for the treatment of tinea pedis. In some embodiments the compositions disclosed herein include at least one anti-fungal agent.

Tinea Versicolor

Tinea versicolor is a chronic fungal infection of the skin and is characterized as a rash in humans known to be caused by pitryosporum and two species of malassezia genus yeast: malassezia globosa and malassezia furfur (Crespo-Erchiga V, Florencio V D. Malassezia yeasts and pityriasis versicolor. Curr Opin Infect Dis. April 2006; 19(2):139-47; Gaitanis G, Velegraki A, Alexopoulos E C, Chasapi V, Tsigonia A, Katsambas A. Distribution of Malassezia species in pityriasis versicolor and seborrhoeic dermatitis in Greece. Typing of the major pityriasis versicolor isolate *M. globosa*. Br J Dermatol. May 2006; 154(5):854-9; Morishita N, Sei Y, Sugita T. Molecular analysis of malassezia microflora from patients with pityriasis versicolor. Mycopathologia. February 2006; 161(2):61-5; Rincon S, Celis A, Sopo L, Motta A, Cepero de Garcia M C. Malassezia yeast species isolated from patients with dermatologic lesions. Biomedica. June 2005; 25(2):189-95; Krisanty R I, Bramono K, Made Wisnu I. Identification of Malassezia species from pityriasis versicolor in Indonesia and its relationship with clinical characteristics. Mycoses. May 2009; 52(3):257-62). Treatment consists of applying antifungal medicines to the skin. These medications include clotrimazole, ketoconazole, and miconazole.

In some embodiments, the compositions and methods described herein are useful for the treatment of tinea versicolor. In some embodiments, the methods described herein are useful for the treatment of tinea versicolor. In some embodiments, the compositions disclosed herein include at least one anti-fungal agent.

Psoriasis

According to the National Institutes of Health (NIH), approximately 2.2% of the United States population have psoriasis (http://emedicine.medscape.com/article/1943419-overview#a0156). Psoriasis is characterized by red scaly elevated plaques which are often located on elbows and knees but can be extensively spread out on the skin of the trunk, limbs, and scalp. This is a chronic, often recurrent, condition which usually begins in early adulthood and lasts the lifetime. Sometimes children are affected. The rash can be uncomfortable, unsightly, and embarrassing.

The pathogenesis of psoriasis is not well understood. Current understanding suggests immune system activation leading to inflammatory changes in the skin. Current methods of treatment seek to reverse the inflammatory changes and reduce the overgrowth thickening of the affected skin areas.

Topical treatment includes use of anti-inflammatory agents (such as corticosteroids to reduce the inflammation in the skin) and antiproliferative agents (such as calcipotriene to reduce the skin overgrowth). Topical agents often have limited effectiveness due to inadequate percutaneous drug delivery through the thickened psoriatic skin. To overcome this obstacle, a topical agent can be covered over with an air impermeable plastic sheet (Saran Wrap™) to increase percutaneous drug delivery. While effective, it is very uncomfortable to wear leading to poor compliance and thus inadequate efficacy.

Oral or systemic agents include anti-inflammatory agents (such as methotrexate, or cyclosporine), and tumor necrosis factor inhibitors (etenercept, infliximab, and similar others). While effective they can damage blood and liver and pose risks of severe toxicity including death. Other modes of therapy include ultraviolet light treatment to suppress epidermal growth (however, one drawback of this treatment is the potential to cause cancer of the skin) and corticosteroid injections into patch suppresses inflammation locally (this is very uncomfortable and can lead to unsightly thinning where injected).

In some embodiments, the compositions and methods described herein are useful for the treatment of psoriasis. In some embodiments the compositions disclosed herein include at least one anti-inflammatory agent. In some embodiments the compositions disclosed herein include at least one anti-proliferative agent.

Test for Stinging

An assessment of stinging can be made using a superficial skin abrasion model. When the skin is disrupted by superficial wounds, subsequently applied materials can sting, burn, and irritate. To measure the stinging, standardized wounds can be created in the skin, typically on the forearm, by sequential tape stripping repeated until the glistening layer is reached. This glistening layer corresponds to the skin's dermal layer where nerves are located. Materials to be tested on the superficial wounds would include a positive control material, such 70% ethanol solution, a negative control, such as the formulation vehicle without active agents, and the test formulation(s). Each material is applied to a single site on the abraded forearm for a short duration of time, such as 15 seconds. The study subject is then asked to rate the intensity of stinging/burning using a predesignated multi-point scale. Thus, stinging as well as burning sensations can be assessed by this method.

For example, in a study of novel first aid formulation for wounds, standardized wounds were created by sequential tape stripping repeated until the glistening layer was reached (Pagnoni A, Spinelli G, Berger R S, Bowman J, Garreffa S, Snoddy A M. Lack of burning and stinging from a novel first aid formulation applied to experimental wounds. *J. Cosmet. Sci*. March-April 2004; 55(2):157-62). Each material to be tested was applied to a wound for 15 seconds. The 24 subjects in the study reported the intensity of the stinging/burning sensation. The tested materials included 70% isopropyl alcohol (sting/burn control), sterile 0.9% sodium chloride solution (no sting/no burn control) and the novel formulation. It was found that the alcohol stung while the novel formulation stung no more than the saline solution.

In another example, irritation of superficial wounds by topical agents commonly used in wound care was assessed using this superficial skin abrasion model (Trookman N S, Rizer R L, Weber T. J. *Amer. Acad. Dermatol*. March 2011; 64(3), Suppl 1:S16-22). As in the previous example, the skin was prepared by sequential tape stripping prior to topical application of the materials in the study.

Methods of Treatment

One embodiment provides a method of treating a skin disease or disorder in an individual comprising topical application to the skin of a subject in need thereof of a pharmaceutical composition suitable for topical administration comprising from about 2% to no more than 59.9% of an alcohol by volume and at least one excipient wherein said composition is a non-homogeneous semisolid and the alcohol is selected from ethanol, isopropanol, or n-propanol. One embodiment provides a method of treating a skin disease or disorder in an individual comprising topical application of a pharmaceutical composition suitable for topical administration comprising from about 2% to no more than 59.9% ethanol by volume, and at least one excipient wherein the composition is a non-homogeneous semisolid. Another embodiment provides the method wherein the composition is a non-homogenous semisolid dispersion. One embodiment provides a method of treating a skin disease or disorder in an individual comprising topical application to the skin of a subject in need thereof of a pharmaceutical composition suitable for topical administration comprising from about 2% to no more than 59.9% of an alcohol by volume and at least one excipient wherein said composition is a non-homogeneous emulsion and the alcohol is selected from ethanol, isopropanol, or n-propanol. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogeneous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion.

Another embodiment provides a method of treating a skin disease or disorder in an individual comprising topical application of a pharmaceutical composition suitable for topical administration comprising from about 2% to no more than 59.9% ethanol by volume, and at least one excipient wherein the composition is a non-homogeneous semisolid and the method is for maintenance therapy. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion.

Another embodiment provides a method of treating a skin disease or disorder in an individual comprising topical application of a pharmaceutical composition suitable for topical administration comprising from about 2% to no more than 59.9% ethanol by volume, and at least one excipient wherein the composition is a non-homogeneous semisolid and the method is for preventive treatment of the skin disease or disorder. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion.

Another embodiment provides a method of treating a skin disease or disorder in an individual comprising topical application of a pharmaceutical composition suitable for topical administration comprising from about 2% to no more than 59.9% ethanol by volume, and at least one excipient wherein the composition is a non-homogeneous semisolid and the method is for prophylactic treatment of the skin disease or disorder. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion.

Another embodiment provides a method of treating a skin disease or disorder in an individual comprising topical application of a pharmaceutical composition suitable for topical administration comprising from about 2% to no more than 59.9% ethanol by volume, and at least one excipient wherein the composition is a non-homogeneous semisolid and the method is for treatment of acute or sub-acute skin disease or disorder. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion.

Another embodiment provides a method of treating a skin disease or disorder in an individual comprising topical application of a pharmaceutical composition suitable for topical administration comprising from about 2% to no more than 59.9% ethanol by volume, at least one moisturizing ingredient and at least one excipient, wherein the composition is a non-homogeneous semisolid. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion. Non-limiting examples of moisturizing ingredients include glycerin, hydrogenated polyisobutene, cetearyl alcohol, macadamia nut oil, dimethicone, tocopheryl acetate, stearoxytrimethylsilane, stearyl alcohol, and panthenol.

Another embodiment provides the method wherein the composition comprises from about 2% to about 10% ethanol by volume. Another embodiment provides the method wherein the composition comprises about 2% ethanol by volume. Another embodiment provides the method wherein the composition comprises about 3% ethanol by volume. Another embodiment provides the method wherein the composition comprises about 4% ethanol by volume. Another embodiment provides the method wherein the composition comprises about 5% ethanol by volume. Another embodiment provides the method wherein the composition comprises about 6% ethanol by volume. Another embodiment provides the method wherein the composition comprises about 7% ethanol by volume. Another embodiment provides the method wherein the composition comprises about 8% ethanol by volume. Another embodiment provides the method wherein the composition comprises about 9% ethanol by volume. Another embodiment provides the method wherein the composition comprises about 10% ethanol by volume. Another embodiment provides the method wherein the composition comprises from about 6% to about 10% ethanol by volume. Another embodiment provides the method wherein the composition comprises from about 5% to about 10% ethanol by volume.

Another embodiment provides the method wherein the composition comprises from about 10% to about 20% ethanol by volume. Another embodiment provides the method wherein the composition comprises about 11% ethanol by volume. Another embodiment provides the method wherein the composition comprises about 12% ethanol by volume. Another embodiment provides the method wherein the composition comprises about 13% ethanol by volume. Another embodiment provides the method wherein the composition comprises about 14% ethanol by volume. Another embodiment provides the method wherein the composition comprises about 15% ethanol by volume. Another embodiment provides the method wherein the composition comprises about 16% ethanol by volume. Another embodiment provides the method wherein the composition comprises from about 10% to about 15% ethanol by volume. Another embodiment provides the method wherein the composition comprises from about 10% to about 16% ethanol by volume. Another embodiment provides the method wherein the composition comprises from about 10% to about 21% ethanol by volume.

Another embodiment provides the method wherein the composition comprises from about 20% to about 30% ethanol by volume. Another embodiment provides the method wherein the composition comprises from about 21% to about 31% ethanol by volume. Another embodiment provides the method wherein the composition comprises about 25% ethanol by volume. Another embodiment provides the method wherein the composition comprises about 30% ethanol by volume. Another embodiment provides the method wherein the composition comprises about 31% ethanol by volume. Another embodiment provides the method wherein the composition comprises about 32% ethanol by volume. Another embodiment provides the method wherein the composition comprises from about 25% to about 30% ethanol by volume. Another embodiment provides the method wherein the composition comprises from about 30% to about 35% ethanol by volume. Another embodiment provides the method wherein the composition comprises from about 30% to about 40% ethanol by volume. Another embodiment provides the method wherein the composition comprises from about 40% to about 50% ethanol by volume. Another embodiment provides the method wherein the composition comprises from about 50% to about 55% ethanol by volume.

Another embodiment provides the method wherein the composition is non-comedogenic.

Another embodiment provides the method wherein the skin disease or disorder is acne, rosacea, dermatitis, secondarily infected dermatitis, bacterial skin infection, or fungal skin infection. Another embodiment provides the method wherein the skin disease or disorder is dermatitis or eczema. Another embodiment provides the method wherein the skin disease or disorder is atopic dermatitis.

Another embodiment provides the method wherein topical application of the pharmaceutical composition does not irritate the skin. Another embodiment provides the method wherein topical application of the pharmaceutical composition does not cause subjective irritation of the skin. Another embodiment provides the method wherein topical application of the pharmaceutical composition does not cause a stinging sensation.

Another embodiment provides a method of treating a skin disease or disorder in an individual by killing or inhibiting the growth of microorganisms. Another embodiment provides the method wherein the microorganisms are bacteria. Examples of such bacteria include Gram positive and Gram negative aerobic and anaerobic bacteria. Non-limiting examples of such bacteria include *Acinetobacter baumannii, Acinetobacter johnsonii, Acinetobacter lwoffi, Corynebacterium* spp., *Enterobacter agglomerans, Enterobacter cloacae, Klebsiella pneumoniae, Propionibacterium acnes, Pseudomonas aeruginosa, Staphylococcus aureus, Staphylococcus epidermidis, Staphylococcus warneri, Streptococcus mitis,* and *Streptococcus pyogenes*. Another embodiment provides the method wherein the microorganisms are fungi. Non-limiting examples of such fungi include *Candida albicans, Trichophyton mentagrophytes, Trichophyton rubrum, Epidermophyton floccosum, Microsporum audouinii, Microsporum canis, Microsporum fulvum, Microsporum gypseum,* and *Pityrosporum ovale.*

Another embodiment provides a method of treating a skin disease or disorder in an individual comprising topical application of a pharmaceutical composition suitable for topical administration comprising from about 2% to no more than 59.9% isopropanol by volume, and at least one excipient wherein the composition is a non-homogeneous semisolid. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion. Another embodiment provides the method wherein the composition comprises from about 2% to about 10% isopropanol by volume. Another embodiment provides the method wherein the composition comprises from about 10% to about 20% isopropanol by volume. Another embodiment provides the method wherein the composition comprises from about 20% to about 30% isopropanol by volume. Another embodiment provides the method wherein the composition comprises from about 30% to about 40% isopropanol by volume. Another embodiment provides the method wherein the composition comprises from about 40% to about 50% isopropanol by volume. Another embodiment provides the method wherein the composition comprises from about 50% to about 59.9% isopropanol by volume.

Methods of Treatment with a Second Active Ingredient

One embodiment provides a means of applying ethanol to the skin without stinging.

One embodiment provides a method of treating a skin disease or disorder in an individual in need thereof comprising topical application to the individual of a chemical matrix comprising from about 2% to about 30% of an alcohol by volume, a corticosteroid and at least one excipient, wherein the chemical matrix is an ointment suitable for topical administration, the alcohol is primarily dispersed into the chemical matrix in the form of microbubbles, and the alcohol is selected from ethanol, isopropanol, or n-propanol.

Another embodiment provides the method wherein the alcohol is ethanol. Another embodiment provides the method wherein the chemical matrix comprises from about 2% to about 10% ethanol by volume. Another embodiment provides the method wherein the chemical matrix comprises from about 10% to about 20% ethanol by volume. Another embodiment provides the method wherein the chemical matrix comprises from about 20% to about 30% ethanol by volume.

Another embodiment provides the method wherein the ointment is selected from aquaphore, white petrolatum USP, white ointment USP, hydrophilic petrolatum USP, or hydrophilic ointment USP.

Another embodiment provides the method wherein the corticosteroid is selected from desonide, or mometasone. Another embodiment provides the method wherein the corticosteroid comprises from about 0.1% (w/w) to about 0.0001% (w/w) of the chemical matrix. Another embodiment provides the method wherein the chemical matrix comprises from about 2% to about 10% ethanol by volume and the corticosteroid is selected from desonide, or mometasone. Another embodiment provides the method wherein the chemical matrix comprises from about 10% to about 20% ethanol by volume and the corticosteroid is selected from desonide, or mometasone. Another embodiment provides the method wherein the chemical matrix comprises from about 20% to about 30% ethanol by volume and the corticosteroid is selected from desonide, or mometasone.

Another embodiment provides the method wherein the chemical matrix comprises from about 2% to about 10% ethanol by volume, the corticosteroid is selected from desonide, or mometasone, and the corticosteroid comprises from about 0.1% (w/w) to about 0.0001% (w/w) of the chemical matrix. Another embodiment provides the method wherein the chemical matrix comprises from about 10% to about 20% ethanol by volume, the corticosteroid is selected from desonide, or mometasone, and the corticosteroid comprises from about 0.1% (w/w) to about 0.0001% (w/w) of the chemical matrix. Another embodiment provides the method wherein the chemical matrix comprises from about 20% to about 30% ethanol by volume, the corticosteroid is selected from desonide, or mometasone, and the corticosteroid comprises from about 0.1% (w/w) to about 0.0001% (w/w) of the chemical matrix.

Another embodiment provides the method wherein the skin disease or disorder is dermatitis. Another embodiment provides the method wherein the skin disease or disorder is eczema. Another embodiment provides the method wherein the skin disease or disorder is atopic dermatitis.

Another embodiment provides the method wherein the alcohol is 1-propanol or 2-propanol. Another embodiment provides the method wherein the corticosteroid is selected from desonide, or mometasone. Another embodiment provides the method wherein the chemical matrix comprises from about 2% to about 10% alcohol by volume. Another embodiment provides the method wherein the chemical matrix comprises from about 10% to about 20% alcohol by volume. Another embodiment provides the method wherein the chemical matrix comprises from about 20% to about 30% alcohol by volume. Another embodiment provides the method wherein the corticosteroid is selected from desonide, or mometasone. Another embodiment provides the method wherein the skin disease or disorder is dermatitis. Another embodiment provides the method wherein the skin disease or disorder is eczema. Another embodiment provides the method wherein the skin disease or disorder is atopic dermatitis.

One embodiment provides a method of treating a skin disease or disorder in an individual comprising topical application of a pharmaceutical composition suitable for topical administration comprising from about 2% to no more than 59.9% of an alcohol by volume, a second active ingredient, and at least one excipient wherein the composition is a non-homogeneous semisolid and the alcohol is selected from ethanol, isopropanol, or n-propanol. One embodiment provides a method of treating a skin disease or disorder in an individual comprising topical application of a pharmaceutical composition suitable for topical administration comprising from about 2% to no more than 59.9% ethanol by volume, a second active ingredient, and at least one excipient wherein the composition is a non-homogeneous semisolid. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment.

One embodiment provides a method of treating a skin disease or disorder in an individual comprising topical application of a pharmaceutical composition suitable for topical administration comprising from about 2% to no more than 59.9% of an alcohol by volume, a second active ingredient, and at least one excipient wherein the composition is a non-homogeneous emulsion and the alcohol is selected from ethanol, isopropanol, or n-propanol. Another embodiment provides a method of treating a skin disease or disorder in an individual comprising topical application of a pharmaceutical composition suitable for topical administration comprising from about 2% to no more than 59.9% ethanol by volume, a second active ingredient, and at least one excipient wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous cream. Another embodiment provides the method wherein the composition is a non-homogenous lotion.

Another embodiment provides the method wherein the composition comprises from about 2% to about 10% ethanol by volume. Another embodiment provides the method wherein the composition comprises about 2% ethanol by volume. Another embodiment provides the method wherein the composition comprises about 3% ethanol by volume. Another embodiment provides the method wherein the composition comprises about 4% ethanol by volume. Another embodiment provides the method wherein the composition comprises about 5% ethanol by volume. Another embodiment provides the method wherein the composition comprises about 6% ethanol by volume. Another embodiment provides the method wherein the composition comprises about 7% ethanol by volume. Another embodiment provides the method wherein the composition comprises about 8% ethanol by volume. Another embodiment provides the method wherein the composition comprises about 9% ethanol by volume. Another embodiment provides the method wherein the composition comprises about 10% ethanol by volume. Another embodiment provides the method wherein the composition comprises from about 6% to about 10% ethanol by volume. Another embodiment provides the method wherein the composition comprises from about 5% to about 10% ethanol by volume.

Another embodiment provides the method wherein the composition comprises from about 10% to about 20% ethanol by volume. Another embodiment provides the method wherein the composition comprises about 11% ethanol by volume. Another embodiment provides the method wherein the composition comprises about 12% ethanol by volume. Another embodiment provides the method wherein the composition comprises about 13% ethanol by volume. Another embodiment provides the method wherein the composition comprises about 14% ethanol by volume. Another embodiment provides the method wherein the composition comprises about 15% ethanol by volume. Another embodiment provides the method wherein the composition comprises about 16% ethanol by volume. Another embodiment provides the method wherein the composition comprises from about 10% to about 15% ethanol by volume. Another embodiment provides the method wherein the composition comprises from about 10% to about 16% ethanol by volume. Another embodiment provides the method wherein the composition comprises from about 10% to about 21% ethanol by volume.

Another embodiment provides the method wherein the composition comprises from about 20% to about 30% ethanol by volume. Another embodiment provides the method wherein the composition comprises from about 21% to about 31% ethanol by volume. Another embodiment provides the method wherein the composition comprises about 25% ethanol by volume. Another embodiment provides the method wherein the composition comprises about 30% ethanol by volume. Another embodiment provides the method wherein the composition comprises about 31% ethanol by volume. Another embodiment provides the method wherein the composition comprises about 32% ethanol by volume. Another embodiment provides the method wherein the composition comprises from about 25% to about 30% ethanol by volume. Another embodiment provides the method wherein the composition comprises from about 30% to about 35% ethanol by volume. Another embodiment provides the method wherein the composition comprises from about 30% to about 40% ethanol by volume. Another embodiment provides the method wherein the composition comprises from about 40% to about 50% ethanol by volume. Another embodiment provides the method wherein the composition comprises from about 50% to about 55% ethanol by volume.

Another embodiment provides the method wherein the composition is non-comedogenic.

Another embodiment provides the method wherein the skin disease or disorder is acne, rosacea, dermatitis, secondarily infected dermatitis, bacterial skin infection, or fungal skin infection. Another embodiment provides the method wherein the skin disease or disorder is dermatitis or eczema. Another embodiment provides the method wherein the skin disease or disorder is atopic dermatitis.

Another embodiment provides the method wherein the second active ingredient is a corticosteroid selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone diacetonide, and triamcinolone hexacetonide; and a pharmaceutically acceptable salt thereof, or phosphate prodrug thereof, or ester prodrug thereof.

Another embodiment provides the method wherein the second active ingredient is a corticosteroid selected from hydrocortisone, desonide, mometasone, betamethasone, fluticasone, fluocinolone, triamcinolone, triamcinolone acetonide, triamcinolone diacetonide, or clobetasol; and a pharmaceutically acceptable salt thereof, or phosphate prodrug thereof, or ester prodrug thereof. Another embodiment provides the pharmaceutical composition wherein the second active ingredient is a corticosteroid selected from hydrocortisone, desonide, mometasone, triamcinolone, triamcinolone acetonide, triamcinolone diacetonide, fluocinolone or fluticasone; and a pharmaceutically acceptable salt thereof, or phosphate prodrug thereof, or ester prodrug thereof. Another embodiment provides the pharmaceutical composition wherein the second active ingredient is hydrocortisone or a pharmaceutically acceptable salt thereof, or phosphate prodrug thereof, or ester prodrug thereof. Another embodiment provides the pharmaceutical composition wherein the second active ingredient is desonide, or a pharmaceutically acceptable salt thereof, or phosphate prodrug thereof, or ester prodrug thereof. Another embodiment provides the pharmaceutical composition wherein the second active ingredient is mometasone. Another embodiment provides the pharmaceutical composition wherein the second active ingredient is fluticasone, or a pharmaceutically acceptable salt thereof, or phosphate prodrug thereof, or ester prodrug thereof. Another embodiment provides the pharmaceutical composition wherein the second active ingredient is fluocinolone. Another embodiment provides the pharmaceutical composition wherein the second active ingredient is triamcinolone.

Another embodiment provides the method wherein the second active ingredient is a corticosteroid. Another embodiment provides the method wherein the second active ingredient is a corticosteroid selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide, or a phosphate or ester prodrug thereof.

Another embodiment provides the method wherein the second active ingredient is a corticosteroid selected from hydrocortisone, desonide, mometasone, betamethasone, fluticasone, triamcinolone, fluocinolone or clobetasol. Another embodiment provides the method wherein the second active ingredient is a corticosteroid selected from hydrocortisone, desonide, mometasone, fluocinolone, triamcinolone or fluticasone. Another embodiment provides the method wherein the second active ingredient is hydrocortisone. Another embodiment provides the method wherein the second active ingredient is desonide. Another embodiment provides the method wherein the second active ingredient is mometasone. Another embodiment provides the method wherein the second active ingredient is fluticasone. Another embodiment provides the method wherein the second active ingredient is fluocinolone. Another embodiment provides the method wherein the second active ingredient is triamcinolone.

Another embodiment provides the method wherein topical application of the pharmaceutical composition does not irritate the skin. Another embodiment provides the method wherein topical application of the pharmaceutical composition does not cause subjective irritation of the skin. Another embodiment provides the method wherein topical application of the pharmaceutical composition does not cause a stinging sensation.

Another embodiment provides a method of treating a skin disease or disorder in an individual comprising topical application of a pharmaceutical composition suitable for topical administration comprising from about 2% to no more than 59.9% isopropanol by volume, a second active ingredient, and at least one excipient wherein the composition is a non-homogeneous semisolid. Another embodiment provides the method wherein the composition is a non-homogenous semisolid dispersion. Another embodiment provides the method wherein the composition is a non-homogenous semisolid emulsion. Another embodiment provides the method wherein the composition is a non-homogenous cream or a non-homogenous ointment. Another embodiment provides the method wherein the composition is a non-homogenous cream. Another embodiment provides the method wherein the composition is a non-homogenous ointment. Another embodiment provides the method wherein the composition is a non-homogeneous emulsion. Another embodiment provides the method wherein the composition is a non-homogenous dispersion. Another embodiment provides the method wherein the composition is a non-homogenous cream or a non-homogenous lotion. Another embodiment provides the method wherein the composition is a non-homogenous lotion. Another embodiment provides the method wherein the composition comprises from about 2% to about 10% isopropanol by volume. Another embodiment provides the method wherein the composition comprises from about 10% to about 20% isopropanol by volume. Another embodiment provides the method wherein the composition comprises from about 20% to about 30% isopropanol by volume. Another embodiment provides the method wherein the composition comprises from about 30% to about 40% isopropanol by volume. Another embodiment provides the method wherein the composition comprises from about 40% to about 50% isopropanol by volume. Another embodiment provides the method wherein the composition comprises from about 50% to about 59.9% isopropanol by volume.

In some of the methods of treatment disclosed herein, the ratio of ethanol to the second active ingredient in the non-homogeneous composition is fixed during the course of treatment. In some of the methods of treatment disclosed herein, the ratio of ethanol to the second active ingredient in the non-homogeneous composition varies as directed by a physician during the course of treatment. Topical application of the non-homogeneous composition can occur one to four times a day or as directed by a physician. The duration of treatment can vary from one to four weeks or as directed by a physician. In some of the methods of treatment disclosed herein, a non-homogeneous composition comprising ethanol and a second active ingredient is topically applied during the initial course of treatment prior to replacement with another non-homogeneous composition comprising ethanol as maintenance therapy. The course of treatment can optionally include pre-treatment of the area with soap and water and/or occlusion of the treatment area subsequent to application of the non-homogeneous composition described herein.

One embodiment provides the method of treating a skin disease or disorder in an individual comprising topical application of a non-homogeneous pharmaceutical composition suitable for topical administration from one to four times a day comprising a fixed ratio of the ethanol and the second active ingredient during the duration of treatment. Another embodiment provides the method wherein the duration of treatment is two weeks. Another embodiment provides the method wherein the duration of treatment is three weeks. Another embodiment provides the method wherein the duration of treatment is four weeks. Another embodiment provides the method wherein the topical administration is once a day. Another embodiment provides the method wherein the topical administration is twice a day. Another embodiment provides the method wherein the topical administration is three times a day. Another embodiment provides the method wherein the topical administration is four times a day.

Another embodiment provides the method of treating a skin disease or disorder in an individual comprising topical application of a pharmaceutical composition suitable for topical administration as directed by a physician comprising a fixed ratio of the ethanol and the second active ingredient during the duration of treatment.

Another embodiment provides the method wherein the non-homogeneous composition comprising a fixed ratio of the ethanol and the second active ingredient contains 5% ethanol by volume. Another embodiment provides the method wherein the non-homogeneous composition comprising a fixed ratio of the ethanol and the second active ingredient contains 6% ethanol by volume. Another embodiment provides the method wherein the non-homogeneous composition comprising a fixed ratio of the ethanol and the second active ingredient contains 7% ethanol by volume. Another embodiment provides the method wherein the non-homogeneous composition comprising a fixed ratio of the ethanol and the second active ingredient contains 10% ethanol by volume. Another embodiment provides the method wherein the non-homogeneous composition comprising a fixed ratio of the ethanol and the second active ingredient contains 12% ethanol by volume. Another embodiment provides the method wherein the non-homogeneous composition comprising a fixed ratio of the ethanol and the second active ingredient contains 16% ethanol by volume. Another embodiment provides the method wherein the non-homogeneous composition comprising a fixed ratio of the ethanol and the second active ingredient contains 21% ethanol by volume. Another embodiment provides the method wherein the non-homogeneous composition comprising a fixed ratio of the ethanol and the second active ingredient contains 31% ethanol by volume.

Another embodiment provides the method of treating a skin disease or disorder in an individual comprising topical application of a non-homogeneous pharmaceutical composition suitable for topical administration from one to four times a day as part of a progressive ratio therapy in which the percentage of ethanol is increased every 2-3 days during the duration of treatment. Another embodiment provides the method wherein the duration of treatment is two weeks. Another embodiment provides the method wherein the duration of treatment is three weeks. Another embodiment provides the method wherein the duration of treatment is four weeks. Another embodiment provides the method wherein the topical administration is once a day. Another embodiment provides the method wherein the topical administration is twice a day. Another embodiment provides the method wherein the topical administration is three times a day. Another embodiment provides the method wherein the topical administration is four times a day. Another embodiment provides the method of treating a skin disease or disorder in an individual comprising topical application of a pharmaceutical composition suitable for topical administration as directed by a physician during the duration of treatment.

Another embodiment provides the method wherein the percentage of ethanol is increased every 2 days during the duration of treatment. Another embodiment provides the method wherein the percentage of ethanol is increased every 3 days during the duration of treatment. Another embodiment provides the method wherein the percentage of ethanol is increased when there is visible improvement of the skin condition during the duration of treatment. Another embodiment provides the method of treating a skin disease or disorder in an individual comprising topical application of a non-homogeneous pharmaceutical composition suitable for topical administration from one to four times a day as part of a progressive ratio therapy in which the percentage of ethanol was increased as directed by a physician during the duration of treatment.

Another embodiment provides the method wherein the initial percentage of ethanol is 5% and the final percentage of ethanol is 31% during the duration of treatment. Another embodiment provides the method wherein the initial percentage of ethanol is 7% and the final percentage of ethanol is 31% during the duration of treatment. Another embodiment provides the method wherein the initial percentage of ethanol is 10% and the final percentage of ethanol is 31% during the duration of treatment. Another embodiment provides the method wherein the initial percentage of ethanol is about 5% to about 10% and the final percentage of ethanol is 31% during the duration of treatment.

Compositions for the Treatment of Skin Diseases and Disorders

The compositions described herein are non-homogenous. In particular, it has been found that when the alcohol, selected from ethanol, propanol, or iso-propanol, is distributed in a non-homogenous fashion throughout the bulk of the composition or matrix into bubble-like regions of locally high concentration, referred to herein as microbubbles, wherein the approximate effective concentration of the alcohol inside the microbubbles is about 60% to about 80%, a beneficial effect is observed upon topical application to damaged skin but without a stinging sensation. In the compositions described herein, a key aspect is the role of the alcohol. The alcohol, selected from ethanol, propanol, or iso-propanol, functions as an active ingredient of the composition having an antiseptic activity and not merely as a solvent or excipient.

In some embodiments, the microbubbles are dispersed into a chemical matrix which is an ointment. In other embodiments, the microbubbles are dispersed into a chemical matrix which is a semi-solid. In other embodiments, the microbubbles are dispersed into a chemical matrix which is a cream.

One embodiment provides a chemical matrix comprising from about 2% to about 30% of an alcohol by volume, a corticosteroid and at least one excipient, wherein the chemical matrix is an ointment suitable for topical administration, the alcohol is primarily dispersed into the chemical matrix in the form of microbubbles, and the alcohol is selected from ethanol, isopropanol, or n-propanol.

Another embodiment provides the chemical matrix wherein the alcohol is ethanol. Another embodiment provides the chemical matrix wherein the chemical matrix comprises from about 2% to about 10% ethanol by volume. Another embodiment provides the chemical matrix wherein the chemical matrix comprises from about 10% to about 20% ethanol by volume. Another embodiment provides the chemical matrix wherein the chemical matrix comprises from about 20% to about 30% ethanol by volume.

Another embodiment provides the chemical matrix wherein the ointment is selected from aquaphore, white petrolatum USP, white ointment USP, hydrophilic petrolatum USP, or hydrophilic ointment USP.

Another embodiment provides the chemical matrix wherein the corticosteroid is selected from desonide, or mometasone. Another embodiment provides the chemical matrix wherein the corticosteroid comprises from about 0.1% (w/w) to about 0.0001% (w/w) of the chemical matrix. Another embodiment provides the chemical matrix wherein the corticosteroid comprises from about 0.1% (w/w) to about 0.001% (w/w) of the chemical matrix. Another embodiment provides the chemical matrix wherein the corticosteroid comprises from about 0.1% (w/w) to about 0.01% (w/w) of the chemical matrix. Another embodiment provides the chemical matrix wherein the corticosteroid comprises from about 0.1% (w/w) to about 0.005% (w/w) of the chemical matrix. Another embodiment provides the chemical matrix wherein the corticosteroid comprises from about 0.1% (w/w) to about 0.05% (w/w) of the chemical matrix. Another embodiment provides the chemical matrix wherein the corticosteroid comprises from about 0.05% (w/w) to about 0.005% (w/w) of the chemical matrix. Another embodiment provides the chemical matrix wherein the chemical matrix comprises from about 2% to about 10% ethanol by volume and the corticosteroid is selected from desonide, or mometasone. Another embodiment provides the chemical matrix wherein the chemical matrix comprises from about 10% to about 20% ethanol by volume and the corticosteroid is selected from desonide, or mometasone. Another embodiment provides the chemical matrix wherein the chemical matrix comprises from about 20% to about 30% ethanol by volume and the corticosteroid is selected from desonide, or mometasone.

Another embodiment provides the chemical matrix wherein the chemical matrix comprises from about 2% to about 10% ethanol by volume, the corticosteroid is selected from desonide, or mometasone, and the corticosteroid comprises from about 0.1% (w/w) to about 0.0001% (w/w) of the chemical matrix. Another embodiment provides the chemical matrix wherein the chemical matrix comprises from about 10% to about 20% ethanol by volume, the corticosteroid is selected from desonide, or mometasone, and the corticosteroid comprises from about 0.1% (w/w) to about 0.0001% (w/w) of the chemical matrix. Another embodiment provides the chemical matrix wherein the chemical matrix comprises from about 20% to about 30% ethanol by volume, the corticosteroid is selected from desonide, or mometasone, and the corticosteroid comprises from about 0.1% (w/w) to about 0.0001% (w/w) of the chemical matrix.

Another embodiment provides the chemical matrix wherein the alcohol is 1-propanol. Another embodiment provides the chemical matrix wherein the corticosteroid is selected from desonide, or mometasone. Another embodiment provides the chemical matrix wherein the chemical matrix comprises from about 2% to about 10% 1-propanol by volume. Another embodiment provides the chemical matrix wherein the chemical matrix comprises from about 10% to about 20% 1-propanol by volume. Another embodiment provides the chemical matrix wherein the chemical matrix comprises from about 20% to about 30% 1-propanol by volume. Another embodiment provides the chemical matrix wherein the corticosteroid is selected from desonide, or mometasone.

Another embodiment provides the chemical matrix wherein the alcohol is 2-propanol. Another embodiment provides the chemical matrix wherein the corticosteroid is selected from desonide, or mometasone. Another embodiment provides the chemical matrix wherein the chemical matrix comprises from about 2% to about 10% 2-propanol by volume. Another embodiment provides the chemical matrix wherein the chemical matrix comprises from about 10% to about 20% 2-propanol by volume. Another embodiment provides the chemical matrix wherein the chemical matrix comprises from about 20% to about 30% 2-propanol by volume. Another embodiment provides the chemical matrix wherein the corticosteroid is selected from desonide, or mometasone. Another embodiment provides the chemical matrix wherein the corticosteroid is selected from desonide, or mometasone. Another embodiment provides the chemical matrix wherein the corticosteroid is selected from desonide, or mometasone.

One embodiment provides a pharmaceutical composition suitable for topical administration comprising from about 2% to no more than 59.9% of an alcohol by volume, a second active ingredient and at least one excipient wherein said composition is a non-homogeneous semisolid and the alcohol is selected from ethanol, isopropanol, or n-propanol. One embodiment provides a pharmaceutical composition suitable for topical administration comprising from about 2% to no more than 59.9% ethanol by volume, a second active ingredient and at least one excipient wherein said composition is a non-homogeneous semisolid. Another embodiment provides the pharmaceutical composition as a semisolid dispersion. Another embodiment provides the pharmaceutical composition as a semisolid emulsion. Another embodiment provides the pharmaceutical composition as a non-homogenous cream or a non-homogenous ointment. Another embodiment provides the pharmaceutical composition as a non-homogenous ointment. Another embodiment provides the pharmaceutical composition as a non-homogenous cream.

One embodiment provides a pharmaceutical composition suitable for topical administration comprising from about 2% to no more than 59.9% of an alcohol by volume, a second active ingredient and at least one excipient wherein said composition is a non-homogeneous emulsion and the alcohol is selected from ethanol, isopropanol, or n-propanol. One embodiment provides a pharmaceutical composition suitable for topical administration comprising from about 2% to no more than 59.9% ethanol by volume, a second active ingredient and at least one excipient wherein said composition is a non-homogenous emulsion. Another embodiment provides the pharmaceutical composition as a dispersion. Another embodiment provides the pharmaceutical composition as a non-homogenous cream or a non-homogenous lotion. Another embodiment provides the pharmaceutical composition as a non-homogenous lotion. Another embodiment provides the pharmaceutical composition as a non-homogenous cream.

Another embodiment provides the pharmaceutical composition wherein the second active ingredient is selected from salicylic acid, glycolic acid, benzoyl peroxide, sulfur, resorcinol, tretinoin, adapalene, tazarotene, clindamycin or erythromycin. Another embodiment provides the pharmaceutical composition wherein the second active ingredient is selected from salicylic acid, glycolic acid, benzoyl peroxide, sulfur, resorcinol, tretinoin, adapalene, tazarotene, clindamycin, erythromycin, metronidazole, or azelaic acid. Another embodiment provides the pharmaceutical composition wherein the second active ingredient is selected from salicylic acid, terbenafine, econazole, miconazole, clotrimazole, butenafine, or tolnaftate. Another embodiment provides the pharmaceutical composition wherein the second active is not menthol.

Another embodiment provides the pharmaceutical composition wherein the second active ingredient is a corticosteroid. Another embodiment provides the pharmaceutical composition wherein the second active ingredient is selected from a corticosteroid, tar derivatives, salicylic acid, calcipotriene, or anthralin.

Another embodiment provides the pharmaceutical composition wherein the second active ingredient is a corticosteroid selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, flu- prednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone diacetonide, and triamcinolone hexacetonide; and a pharmaceutically acceptable salt thereof, or phosphate prodrug thereof, or ester prodrug thereof.

Another embodiment provides the pharmaceutical composition wherein the second active ingredient is a corticosteroid selected from hydrocortisone, desonide, mometasone, betamethasone, fluticasone, fluocinolone, triamcinolone, triamcinolone acetonide, triamcinolone diacetonide, or clobetasol; and a pharmaceutically acceptable salt thereof, or phosphate prodrug thereof, or ester prodrug thereof. Another embodiment provides the pharmaceutical composition wherein the second active ingredient is a corticosteroid selected from hydrocortisone, desonide, mometasone, triamcinolone, triamcinolone acetonide, triamcinolone diacetonide, fluocinolone or fluticasone; and a pharmaceutically acceptable salt thereof, or phosphate prodrug thereof, or ester prodrug thereof. Another embodiment provides the pharmaceutical composition wherein the second active ingredient is hydrocortisone or a pharmaceutically acceptable salt thereof, or phosphate prodrug thereof, or ester prodrug thereof. Another embodiment provides the pharmaceutical composition wherein the second active ingredient is desonide, or a pharmaceutically acceptable salt thereof, or phosphate prodrug thereof, or ester prodrug thereof. Another embodiment provides the pharmaceutical composition wherein the second active ingredient is mometasone. Another embodiment provides the pharmaceutical composition wherein the second active ingredient is fluticasone, or a pharmaceutically acceptable salt thereof, or phosphate prodrug thereof, or ester prodrug thereof. Another embodiment provides the pharmaceutical composition wherein the second active ingredient is fluocinolone. Another embodiment provides the pharmaceutical composition wherein the second active ingredient is triamcinolone.

The numerous corticosteroids have been classified by several protocols. Classification by chemical structure is known as the Coopman classification and is indicated below.

Group A—Hydrocortisone Type
  hydrocortisone, hydrocortisone acetate, cortisone acetate, tixocortol pivalate, prednisolone, methylprednisolone, and prednisone (short- to medium-acting glucocorticoids)
Group B—Acetonides (and related substances)
  triamcinolone acetonide, triamcinolone alcohol, mometasone, amcinonide, budesonide, desonide, fluocinonide, fluocinolone acetonide, and halcinonide
Group C—Betamethasone Type
  betamethasone, betamethasone sodium phosphate, dexamethasone, dexamethasone sodium phosphate, and fluocortolone
Group D—Esters
Group D1—Halogenated (Less Labile)
  hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate Group D2—Labile Prodrug Esters
  hydrocortisone-17-butyrate, 17-aceponate, 17-buteprate, and prednicarbate The Coopman classification is particularly useful in cases where a certain corticosteroid serves an allergen. In this situation allergic reactions to one member of a class typically indicate an intolerance of all members of the class.

An alternative classification protocol involves grouping by strength in an standard vasoconstriction assay (Ference and Last, Am Fam Physician. 2009, Jan. 15; 79(2):135-140). In this protocol, seven potency groups have been established ranging from high potency to low potency.

Ultra high (I) Augmented betamethasone dipropionate 0.05%
  Clobetasol propionate 0.05%
  Diflorasone diacetate 0.05%
  Fluocinonide 0.1%
  Flurandrenolide 0.05%
High (II) Amcinonide 0.1%
  Augmented betamethasone dipropionate 0.05%
  Betamethasone dipropionate 0.05%
  Desoximetasone 0.25%
  Diflorasone diacetate 0.05%
  Fluocinonide 0.05%
  Halcinonide 0.1%
  Halobetasol propionate 0.05%
Medium to high (III) Amcinonide 0.1%
  Betamethasone dipropionate 0.05%
  Fluticasone propionate 0.005%
  Triamcinolone acetonide 0.5%
  Halobetasol propionate 0.05%
Medium (IV and V) Betamethasone valerate 0.1%
  Desoximetasone 0.05%
  Fluocinolone acetonide 0.025%
  Fluticasone propionate 0.05%
  Hydrocortisone butyrate 0.1%
  Hydrocortisone probutate 0.1%
  Hydrocortisone valerate 0.2%
  Mometasone furoate 0.1%
  Triamcinolone acetonide 0.025%
  Triamcinolone acetonide 0.1%
Low (VI) Alclometasone dipropionate 0.05%
  Desonide 0.05%
  Fluocinolone 0.01%
  Hydrocortisone butyrate 0.1%
Least potent (VII) Hydrocortisone 1%, 2.5%

Ultra-high-potency topical steroids should not be used continuously for longer than three weeks. Low- to high-potency topical steroids should not be used continuously for longer than three months to avoid side effects. Prolonged use of topical corticosteroids may cause side effects. To reduce the risk, the least potent steroid should be used for the shortest time, while still maintaining effectiveness.

In addition to allowing for the use of an antiseptic alcohol, such as ethanol, 1-propanol, or 2-propanol, in a manner which avoids stinging when applied to cracked or damaged skin, the compositions and methods described herein allow for the use of corticosteroids at lower concentrations than previously employed while maintaining efficacy. The benefits derived from this treatment regimen at lower doses of corticosteroid are several. First, a lower dose or exposure level of corticosteroid will result in fewer side effects from corticosteroid use. Second, if lower doses or exposure levels are possible, the attending physician may elect to use a more potent corticosteroid for difficult to treat cases. Also, the use of the more potent corticosteroid may allow for faster resolution of dermatological condition and an overall shortening of the period of time during which the patient is undergoing therapy. Thus, one advantage of the compositions and methods described herein is that the compositions described herein provide equal or greater efficacy than currently accepted treatments but at a lower exposure level of corticosteroid to the patient.

In some embodiments, the amount of corticosteroid present in the formulation is equivalent to the FDA approved wt %. In other embodiments, the amount of corticosteroid present in the formulation is about 100% of the FDA approved wt %. In other embodiments, the amount of corticosteroid present in the formulation is about 90% of the FDA approved wt %. In other embodiments, the amount of corticosteroid present in the formulation is about 80% of the FDA approved wt %. In other embodiments, the amount of corticosteroid present in the formulation is about 70% of the FDA approved wt %. In other embodiments, the amount of corticosteroid present in the formulation is about 60% of the FDA approved wt %. In other embodiments, the amount of corticosteroid present in the formulation is about 50% of the FDA approved wt %. In other embodiments, the amount of corticosteroid present in the formulation is about 40% of the FDA approved wt %. In other embodiments, the amount of corticosteroid present in the formulation is about 30% of the FDA approved wt %. In other embodiments, the amount of corticosteroid present in the formulation is about 20% of the FDA approved wt %. In other embodiments, the amount of corticosteroid present in the formulation is about 10% of the FDA approved wt %. In other embodiments, the amount of corticosteroid present in the formulation is about 5% of the FDA approved wt %. In other embodiments, the amount of corticosteroid present in the formulation is about 4% of the FDA approved wt %. In other embodiments, the amount of corticosteroid present in the formulation is about 3% of the FDA approved wt %. In other embodiments, the amount of corticosteroid present in the formulation is about 2% of the FDA approved wt %. In other embodiments, the amount of corticosteroid present in the formulation is about 1% of the FDA approved wt %.

A feature of the non-homogenous chemical matrices and compositions described herein is the compartmentalized or segregated nature of the matrices and compositions. As described herein the alcohol, selected from ethanol, 1-propanol or 2-propanol, is located primarily within the microbubbles and the microbubbles are dispersed into the chemical matrix. The corticosteroid or other second active ingredient, however, is dispersed primarily in the chemical matrix and is not found substantially within the microbubbles. In some embodiments, at least 95% of the alcohol is located within the microbubble. In some embodiments, at least 90% of the alcohol is located within the microbubble. In some embodiments, at least 85% of the alcohol is located within the microbubble. In some embodiments, at least 80% of the alcohol is located within the microbubble. In some embodiments, at least 75% of the alcohol is located within the microbubble. In some embodiments, at least 70% of the alcohol is located within the microbubble. In some embodiments, at least 65% of the alcohol is located within the microbubble. In some embodiments, at least 60% of the alcohol is located within the microbubble. In some embodiments, at least 55% of the alcohol is located within the microbubble. In some embodiments, at least 50% of the alcohol is located within the microbubble.rd Another embodiment provides the pharmaceutical composition wherein the composition comprises about 2% ethanol by volume. Another embodiment provides the pharmaceutical composition wherein the composition comprises about 3% ethanol by volume. Another embodiment provides the pharmaceutical composition wherein the composition comprises about 4% ethanol by volume. Another embodiment provides the pharmaceutical composition wherein the composition comprises about 5% ethanol by volume. Another embodiment provides the pharmaceutical composition wherein the composition comprises about 6% ethanol by volume. Another embodiment provides the pharmaceutical composition wherein the composition comprises about 7% ethanol by volume. Another embodiment provides the pharmaceutical composition wherein the composition comprises about 8% ethanol by volume. Another embodiment provides the pharmaceutical composition wherein the composition comprises about 9% ethanol by volume. Another embodiment provides the pharmaceutical composition wherein the composition comprises about 10% ethanol by volume. Another embodiment provides the pharmaceutical composition wherein the composition comprises from about 6% to about 10% ethanol by volume. Another embodiment provides the pharmaceutical composition wherein the composition comprises from about 2% to about 10% ethanol by volume. Another embodiment provides the pharmaceutical composition wherein the composition comprises from about 5% to about 10% ethanol by volume.

Another embodiment provides the pharmaceutical composition wherein the composition comprises from about 10% to about 20% ethanol by volume. Another embodiment provides the pharmaceutical composition wherein the composition comprises about 11% ethanol by volume. Another embodiment provides the pharmaceutical composition wherein the composition comprises about 12% ethanol by volume. Another embodiment provides the pharmaceutical composition wherein the composition comprises about 13% ethanol by volume. Another embodiment provides the pharmaceutical composition wherein the composition comprises about 14% ethanol by volume. Another embodiment provides the pharmaceutical composition wherein the composition comprises about 15% ethanol by volume. Another embodiment provides the pharmaceutical composition wherein the composition comprises about 16% ethanol by volume. Another embodiment provides the pharmaceutical composition wherein the composition comprises from about 10% to about 15% ethanol by volume. Another embodiment provides the pharmaceutical composition wherein the composition comprises from about 10% to about 16% ethanol by volume. Another embodiment provides the pharmaceutical composition wherein the composition comprises from about 10% to about 21% ethanol by volume.

Another embodiment provides the pharmaceutical composition wherein the composition comprises from about 20% to about 30% ethanol by volume. Another embodiment provides the method wherein the composition comprises from about 21% to about 31% ethanol by volume. Another embodiment provides the pharmaceutical composition wherein the composition comprises about 25% ethanol by volume. Another embodiment provides the pharmaceutical composition wherein the composition comprises about 30% ethanol by volume. Another embodiment provides the pharmaceutical composition wherein the composition comprises about 31% ethanol by volume. Another embodiment provides the pharmaceutical composition wherein the composition comprises about 32% ethanol by volume. Another embodiment provides the pharmaceutical composition wherein the composition comprises from about 25% to about 30% ethanol by volume. Another embodiment provides the pharmaceutical composition wherein the composition comprises from about 30% to about 35% ethanol by volume. Another embodiment provides the pharmaceutical composition wherein the composition comprises from about 30% to about 40% ethanol by volume.

Another embodiment provides the pharmaceutical composition wherein the composition comprises from about 40% to about 50% ethanol by volume. Another embodiment provides the pharmaceutical composition wherein the composition comprises from about 50% to about 55% ethanol by volume.

All non-homogeneous pharmaceutical compositions comprising ethanol disclosed herein do not contain greater than 59.9% ethanol.

Another embodiment provides the pharmaceutical composition wherein the composition is non-comedogenic.

Another embodiment provides the pharmaceutical composition wherein topical application of the pharmaceutical composition does not irritate the skin. Another embodiment provides the pharmaceutical composition wherein topical application of the pharmaceutical composition does not cause subjective irritation of the skin. Another embodiment provides the pharmaceutical composition wherein topical application of the pharmaceutical composition does not cause a stinging sensation.

The compositions described herein contain alcohols which provide an antiseptic effect when applied to the skin in high concentrations. By virtue of the non-homogenous nature of the compositions described herein, topical application of these compositions does not produce a stinging sensation when applied to the skin. These alcohols are selected from ethanol, isopropanol (2-propanol), or n-propanol (1-propanol), (Kampf et al, Clin. Microbiol. Rev. (2004), 17(4), 863-93; Federal Register Vol. 47, No. 99, Friday, May 21, 1982, pages 22324-22333). Based on the disclosure provided herein a skilled practitioner can prepare and use the compositions described herein comprising ethanol, isopropanol or n-propanol. For the compositions containing isopropanol the approximate effective concentration in the bubble-like regions of locally high concentration is about 60% to about 80%. For the compositions containing n-propanol the approximate effective concentration in the bubble-like regions of locally high concentration is about 60% to about 80%.

One embodiment provides a pharmaceutical composition suitable for topical administration comprising from about 2% to no more than 59.9% isopropanol by volume, a second active ingredient and at least one excipient wherein said composition is a non-homogeneous semisolid. Another embodiment provides the pharmaceutical composition as a semisolid dispersion. Another embodiment provides the pharmaceutical composition as a semisolid emulsion. Another embodiment provides the pharmaceutical composition as a non-homogenous cream or a non-homogenous ointment. Another embodiment provides the pharmaceutical composition as a non-homogenous ointment. Another embodiment provides the pharmaceutical composition as a non-homogenous cream.

One embodiment provides a pharmaceutical composition suitable for topical administration comprising from about 2% to no more than 59.9% isopropanol by volume, a second active ingredient and at least one excipient wherein said composition is a non-homogenous emulsion. Another embodiment provides the pharmaceutical composition as a dispersion. Another embodiment provides the pharmaceutical composition as a non-homogenous cream or a non-homogenous lotion. Another embodiment provides the pharmaceutical composition as a non-homogenous lotion. Another embodiment provides the pharmaceutical composition as a non-homogenous cream.

Another embodiment provides the composition wherein the composition comprises from about 2% to about 10% isopropanol by volume. Another embodiment provides the composition wherein the composition comprises from about 10% to about 20% isopropanol by volume. Another embodiment provides the composition wherein the composition comprises from about 20% to about 30% isopropanol by volume. Another embodiment provides the composition wherein the composition comprises from about 30% to about 40% isopropanol by volume. Another embodiment provides the composition wherein the composition comprises from about 40% to about 50% isopropanol by volume. Another embodiment provides the composition wherein the composition comprises from about 50% to about 59.9% isopropanol by volume. All non-homogeneous pharmaceutical compositions comprising isopropanol disclosed herein do not contain greater than 59.9% isopropanol.

One embodiment provides a pharmaceutical composition suitable for topical administration comprising from about 2% to no more than 59.9% n-propanol by volume, a second active ingredient and at least one excipient wherein said composition is a non-homogeneous semisolid. Another embodiment provides the pharmaceutical composition as a semisolid dispersion. Another embodiment provides the pharmaceutical composition as a semisolid emulsion. Another embodiment provides the pharmaceutical composition as a non-homogenous cream or a non-homogenous ointment. Another embodiment provides the pharmaceutical composition as a non-homogenous ointment. Another embodiment provides the pharmaceutical composition as a non-homogenous cream.

One embodiment provides a pharmaceutical composition suitable for topical administration comprising from about 2% to no more than 59.9% n-propanol by volume, a second active ingredient and at least one excipient wherein said composition is a non-homogenous emulsion. Another embodiment provides the pharmaceutical composition as a dispersion. Another embodiment provides the pharmaceutical composition as a non-homogenous cream or a non-homogenous lotion. Another embodiment provides the pharmaceutical composition as a non-homogenous lotion. Another embodiment provides the pharmaceutical composition as a non-homogenous cream.

Another embodiment provides the composition wherein the composition comprises from about 2% to about 10% n-propanol by volume. Another embodiment provides the composition wherein the composition comprises from about 10% to about 20% n-propanol by volume. Another embodiment provides the composition wherein the composition comprises from about 20% to about 30% n-propanol by volume. Another embodiment provides the composition wherein the composition comprises from about 30% to about 40% n-propanol by volume. Another embodiment provides the composition wherein the composition comprises from about 40% to about 50% n-propanol by volume. Another embodiment provides the composition wherein the composition comprises from about 50% to about 59.9% n-propanol by volume. All non-homogeneous pharmaceutical compositions comprising n-propanol disclosed herein do not contain greater than 59.9% n-propanol.

In some embodiments, a pharmaceutical composition suitable for topical administrations described herein exhibits a viscosity of between about 10,000 and about 1,000,000 centipoise. In some embodiments, a pharmaceutical composition suitable for topical administrations described herein exhibits a viscosity of between about 50,000 and about 1,000,000 centipoise. In some embodiments, a pharmaceutical composition suitable for topical administrations described herein exhibits a viscosity of between about 150,000 and about 1,000,000 centipoise. In some embodiments, a pharmaceutical composition suitable for topical administrations described herein exhibits a viscosity of between about 50,000 and about 600,000 centipoise. In some embodiments, a pharmaceutical composition suitable for topical administrations described herein exhibits a viscosity of between about 100,000 and about 500,000 centipoise. The viscosity is measured at a shear rate of $0.31$ $s^{-1}$ using a cone/plate viscometer (Brookfield DVII+Pro viscometer with a CP50 spindle at 0.08 rpm as a reference).

The compositions described herein are prepared by methods well known in the art of pharmacy described in standard texts, such as *Remington: The Science and Practice of Pharmacy*, Nineteenth Ed (Easton, Pa.: Mack Publishing Company, 1995). The processes for preparing the non-homogenous compositions described herein are performed with agitators, mechanical mixers, colloid mills homogenizers, ultrasonic devices, microfluidizers and the like. In some embodiments the bubble-like regions of locally high ethanol concentration can be viewed with the unaided eye. In other embodiments, the bubble-like regions of locally high ethanol concentrations require the use of a microscope to visualize.

Pharmaceutically Acceptable Salts and Prodrugs

"Pharmaceutically acceptable salt" includes both acid and base addition salts. A pharmaceutically acceptable salt of any one of the corticosteriods described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar. In some embodiments, the corticosteroid salts are selected from acetate, diacetate, propionate, dipropionate, valerate, pivalate, diacetate, or butyrate salts.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

In some embodiments, the corticosteroids described herein are administered as phosphate prodrugs. In some embodiments, the corticosteroids described herein are administered as sodium phosphate prodrugs. In some embodiments, the corticosteroids described herein are administered as ester prodrugs. In some embodiments, the corticosteroids described herein are administered as acetyl, diacetyl, propanoate, dipropionate, pivalate, valerate, butyrate, butyl, furoate, or ethoxycarbonyl ester prodrugs.

Excipients

Disclosed herein, in some embodiments, is a composition formulated as a non-homogenous ointment. In some embodiments, the ointment is aquaphore. In some embodiments, the ointment base is a hydrocarbon base selected from white petrolatum, USP or white ointment, USP. In some embodiments, the ointment base is an absorption base selected from hydrophilic petrolatum, USP or lanolin, USP. In some embodiments, the ointment base is water-removable base, such as hydrophilic ointment, USP. In some embodiments, the ointment base is a water-soluble base, such as polyethylene glycol ointment, NF.

Disclosed herein, in some embodiments, is a pharmaceutical composition wherein the composition is a non-homogenous lotion or a non-homogenous cream. The hydrophobic component of a lotion or cream is derived from an animal (e.g., lanolin, cod liver oil, and ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly).

The compositions described herein are not foams.

Disclosed herein, in certain embodiments, is a pharmaceutical composition wherein the composition comprises a thickening agent. In some embodiments, the composition disclosed herein further comprises from about 0.1% to about 5%, more preferably from about 0.1% to about 3%, and most preferably from about 0.25% to about 2%, of a thickening agent.

In some embodiments, the excipient is selected from celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof. In some embodiments, the excipient is not a polysiloxane.

Disclosed herein, in some embodiments, is a pharmaceutical composition wherein the composition comprises an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

Disclosed herein, in some embodiments, is a pharmaceutical composition wherein the composition comprises essential oils, fragrances, skin-conditioning agents, skin healing agents, skin protectants (e.g., sunscreens, or ultraviolet light absorbers or scattering agents), skin soothing agents, preservatives or combinations thereof.

Pharmaceutical compositions disclosed herein are formulated in any suitable manner. Any suitable technique, carrier, and/or excipient is contemplated for use with the non-homogenous compositions disclosed herein. For a summary of pharmaceutical topical formulations described herein see *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Eighth Ed. (Lippincott Williams & Wilkins 2004), Muller, R. H. et al. Advanced Drug Delivery Reviews 59 (2007) 522-530, which are herein incorporated by reference for such disclosures.

Device for the Treatment of Skin Diseases and Disorders

Another embodiment provides a device to be used by the patient prior to topical application of the therapeutic pharmaceutical composition disclosed herein wherein said device contains two reservoirs: a first reservoir containing a first pharmaceutical composition comprising ethanol a second reservoir containing a second pharmaceutical composition comprising a second active agent. Another embodiment provides the device in which said first and second pharmaceutical compositions from said reservoirs are mixed by said device prior to topical application of the therapeutic pharmaceutical composition. Another embodiment provides the device in which said first and second pharmaceutical compositions from said reservoirs are mixed by said device prior to topical application of the therapeutic pharmaceutical composition such that topical application of said therapeutic pharmaceutical composition does not irritate the skin. Another embodiment provides the device in which said first and second pharmaceutical compositions from said reservoirs are mixed by said device prior to topical application of the therapeutic pharmaceutical composition such that topical application of said therapeutic pharmaceutical composition does not cause subjective irritation of the skin. Another embodiment provides the device in which said first and second pharmaceutical compositions from said reservoirs are mixed by said device prior to topical application of the therapeutic pharmaceutical composition such that topical application of said therapeutic pharmaceutical composition does not cause a stinging sensation.

Another embodiment provides the device wherein the therapeutic pharmaceutical composition is a non-homogeneous semisolid pharmaceutical composition suitable for topical administration comprising from about 2% to no more than 59.9% ethanol by volume, at least one excipient, and a second active ingredient. Another embodiment provides the device wherein the therapeutic pharmaceutical composition is a non-homogenous semisolid dispersion. Another embodiment provides the device wherein the therapeutic pharmaceutical composition is a non-homogenous semisolid emulsion. Another embodiment provides the device wherein the therapeutic pharmaceutical composition is a non-homogenous ointment or a non-homogenous cream. Another embodiment provides the device wherein the therapeutic pharmaceutical composition is a non-homogenous ointment. Another embodiment provides the device wherein the therapeutic pharmaceutical composition is a non-homogenous cream.

Another embodiment provides the device wherein the therapeutic pharmaceutical composition is a non-homogeneous emulsion pharmaceutical composition suitable for topical administration comprising from about 2% to no more than 59.9% ethanol by volume, at least one excipient, and a second active ingredient. Another embodiment provides the device wherein the therapeutic pharmaceutical composition is a dispersion. Another embodiment provides the device wherein the therapeutic pharmaceutical composition is a non-homogenous lotion or a non-homogenous cream. Another embodiment provides the device wherein the therapeutic pharmaceutical composition is a non-homogenous lotion. Another embodiment provides the device wherein the therapeutic pharmaceutical composition is a non-homogenous cream.

Another embodiment provides the device wherein the second active ingredient is selected from salicylic acid, glycolic acid, benzoyl peroxide, sulfur, resorcinol, tretinoin, adapalene, tazarotene, clindamycin or erythromycin. Another embodiment provides the device wherein the second active ingredient is selected from salicylic acid, glycolic acid, benzoyl peroxide, sulfur, resorcinol, tretinoin, adapalene, tazarotene, clindamycin, erythromycin, metronidazole, or azelaic acid. Another embodiment provides the device wherein the second active ingredient is selected from salicylic acid, terbenafine, econazole, miconazole, clotrimazole, butenafine, or tolnaftate.

Another embodiment provides the device wherein the second active ingredient is a corticosteroid selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone diacetonide, and triamcinolone hexacetonide; and a pharmaceutically acceptable salt thereof, or phosphate prodrug thereof, or ester prodrug thereof.

Another embodiment provides the device wherein the second active ingredient is a corticosteroid selected from hydrocortisone, desonide, mometasone, betamethasone, fluticasone, fluocinolone, triamcinolone, triamcinolone acetonide, triamcinolone diacetonide, or clobetasol; and a pharmaceutically acceptable salt thereof, or phosphate prodrug thereof, or ester prodrug thereof. Another embodiment provides the pharmaceutical composition wherein the second active ingredient is a corticosteroid selected from hydrocortisone, desonide, mometasone, triamcinolone, triamcinolone acetonide, triamcinolone diacetonide, fluocinolone or fluticasone; and a pharmaceutically acceptable salt thereof, or phosphate prodrug thereof, or ester prodrug thereof. Another embodiment provides the pharmaceutical composition wherein the second active ingredient is hydrocortisone or a pharmaceutically acceptable salt thereof, or phosphate prodrug thereof, or ester prodrug thereof. Another embodiment provides the pharmaceutical composition wherein the second active ingredient is desonide, or a pharmaceutically acceptable salt thereof, or phosphate prodrug thereof, or ester prodrug thereof. Another embodiment provides the pharmaceutical composition wherein the second active ingredient is mometasone. Another embodiment provides the pharmaceutical composition wherein the second active ingredient is fluticasone, or a pharmaceutically acceptable salt thereof, or phosphate prodrug thereof, or ester prodrug thereof. Another embodiment provides the pharmaceutical composition wherein the second active ingredient is fluocinolone. Another embodiment provides the pharmaceutical composition wherein the second active ingredient is triamcinolone.

Another embodiment provides the device wherein the second active ingredient is a corticosteroid. Another embodiment provides the method wherein the second active ingredient is selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide, or a phosphate or ester prodrug thereof.

Another embodiment provides the device wherein the second active ingredient is selected from hydrocortisone, desonide, mometasone, betamethasone, fluticasone, triamcinolone, fluocinolone or clobetasol. Another embodiment provides the device wherein the second active ingredient is hydrocortisone, desonide, mometasone, fluocinolone, triamcinolone or fluticasone. Another embodiment provides the device wherein the second active ingredient is hydrocortisone. Another embodiment provides the device wherein the second active ingredient is desonide. Another embodiment provides the device wherein the second active ingredient is mometasone. Another embodiment provides the device wherein the second active ingredient is fluticasone. Another embodiment provides the device wherein the second active ingredient is fluocinolone. Another embodiment provides the device wherein the second active ingredient is triamcinolone.

Another embodiment provides a device for the preparation of a non-homogenous ethanol containing topical composition wherein the first pharmaceutical composition is a gel, an emulsion, a dispersion, a lotion, a cream, an ointment, or a solution. Another embodiment provides the device wherein the first pharmaceutical composition containing ethanol comprises from about 10% to about 20% ethanol. Another embodiment provides the device wherein the first pharmaceutical composition containing ethanol comprises from about 20% to about 30% ethanol. Another embodiment provides the device wherein the first pharmaceutical composition containing ethanol comprises from about 30% to about 40% ethanol. Another embodiment provides the device wherein the first pharmaceutical composition containing ethanol comprises from about 40% to about 50% ethanol. Another embodiment provides the device wherein the first pharmaceutical composition containing ethanol comprises from about 50% to about 60% ethanol. Another embodiment provides the device wherein the first pharmaceutical composition containing ethanol comprises from about 60% to about 70% ethanol. Another embodiment provides the device wherein the first pharmaceutical composition containing ethanol comprises from about 70% to about 80% ethanol. Another embodiment provides the device wherein the first pharmaceutical composition containing ethanol comprises from about 80% to about 90% ethanol. Another embodiment provides the device wherein the first pharmaceutical composition containing ethanol comprises from about 25% to about 35% ethanol. Another embodiment provides the device wherein the first pharmaceutical composition containing ethanol comprises from about 35% to about 45% ethanol. Another embodiment provides the device wherein the first pharmaceutical composition containing ethanol comprises from about 45% to about 55% ethanol. Another embodiment provides the device wherein the first pharmaceutical composition containing ethanol comprises from about 55% to about 65% ethanol.

Another embodiment provides a device for the preparation of a non-homogenous ethanol containing topical composition wherein said device comprises means for mixing, agitating, shaking, stirring or blending a first pharmaceutical composition with a second pharmaceutical composition. Another embodiment provides a device for the preparation of a non-homogenous ethanol containing topical composition wherein said device comprises containing means for a first pharmaceutical composition, containing means for a second pharmaceutical composition, blending means to produce a non-homogenous composition, and dispensing means. Another embodiment provides the device wherein the blending means is an enclosed chamber. Another embodiment provides the device wherein the blending means is an enclosed chamber and the dispensing means is a contoured opening in the blending chamber.

Another embodiment provides the device wherein the therapeutic pharmaceutical composition is non-comedogenic.

EXAMPLES

I. Preparation of Composition for Topical Administration

Example 1-1

Preparation of an Ethanol Containing Gel

| Ingredient | Quantity |
|---|---|
| ethanol | 62.0 g |
| water | about 35.0 g |
| Carbomer USP | 0.5 g |
| NaOH (10%) | about 2.5 g |

A 100-g batch of ethanol gel formulation is prepared by suspending 0.5 g of carbomer USP in 62 g ethanol and about 30 g of water. The resulting mixture is agitated to ensure complete dissolution. The pH of the solution is adjusted to pH 7 by the addition of about 2.5 g of 10% NaOH solution and the resulting solution is brought to 100 g total mass by the addition of about 5 g of water. The resulting material is packaged in a tube, bottle, or pump dispenser.

Example 1-2

General Procedure for the Preparation of an Ethanol Containing Non-Homogenous Composition with Corticosteroid Corticosteroid ointment and 62% ethanol gel were thoroughly mixed together. Volumes of the 62% ethanol and corticosteroid ointment varied and were dependent on the desired ratio of the two components (see Table 1). The composition was immediately topically applied.

TABLE 1

Sample ratios of corticosteroid ointment to 62% ethanol gel and the corresponding composition percent ethanol by volume

| Ratio of corticosteroid ointment to ethanol gel | Volume of corticosteroid ointment (mL) | Volume of 62% ethanol gel (mL) | Composition percent ethanol by volume (%) |
|---|---|---|---|
| 1:1 | 1.25 | 1.25 | 31 |
| 2:1 | 1.7 | 0.8 | 21 |
| 3:1 | 1.9 | 0.6 | 16 |
| 4:1 | 2.0 | 0.5 | 12 |
| 5:1 | 2.1 | 0.4 | 10 |
| 8:1 | 2.2 | 0.3 | 7 |
| 10:1 | 2.3 | 0.2 | 5 |

Example 1-3

Preparation of an Ethanol Containing Non-Homogenous Composition with Desonide 0.05%

For a 5:1 ratio of desonide 0.05% ointment to 62% ethanol gel: 0.4 mL of 62% ethanol gel and desonide 0.05% ointment (2.1 mL) were thoroughly mixed together. The composition was immediately topically applied.

For a 10:1 ratio of desonide 0.05% ointment to 62% ethanol gel: 0.2 mL of 62% ethanol gel and desonide 0.05% ointment (2.3 mL) were thoroughly mixed together. The composition was immediately topically applied.

Example 1-4

Preparation of an Ethanol Containing Non-Homogenous Composition with Mometasone Furoate 0.1%

Compositions were prepared using the general method presented in Example 1-2.

Example 1-5

Preparation of an Ethanol Containing Composition with Triamcinolone 0.1%

Compositions were prepared using the general method presented in Example 1-2.

Example 1-6

Preparation of an Ethanol Containing Composition with Fluocinolone 0.1%

Compositions were prepared using the general method presented in Example 1-2.

Example 1-7

Preparation of Maintenance Non-Homogenous Lotion Containing Ethanol

Moisturizing lotion, cream or ointment and 62% ethanol gel were thoroughly mixed together. Volumes of the 62% ethanol gel and moisturizing lotion, cream, or ointment varied and were dependent on the desired ratio of the two components. The composition was immediately topically applied.

II. Treatment of Skin Diseases and Disorders

Example 2-1

Treatment of Secondarily Infected Dermatitis

Dermatitis is a common form of red, scaly, itchy patches which frequently is infected due to the patients scratching their itchy areas. Conventional treatment is based on use of topical steroid creams, and oral or topical antibiotics. Treatment often is only partly helpful and patients often are reluctant to use oral antibiotics due to potential side effects. Several patients have presented with secondarily infected dermatitis and participated in the new course of treatment.
  a. Man with hand dermatitis. Treatment with topical mometasone cream and oral antibiotics and topical mupirocin provided partial response over 3 weeks treatment. In an attempt to achieve complete response the patient was treated with a non-homogenous composition comprising mometasone (0.05%) and ethanol (31%); no further oral antibiotics were administered. The patient showed significant improvement in 3 days.
  b. Man with extensive dermatitis over his trunk and limbs with culture proven staphylococcus aureus. Treatment with a non-homogenous composition comprising ethanol (31%) and triamcinolone (0.05%) was far more effective than oral antibiotic therapy (cephalexin) combined with triamcinolone (0.1%) cream. Within 2 days the patient showed significant improvement.
  c. Woman with 20 years of hand dermatitis complicating scleroderma (a form of skin tightening which compromises blood flow). The patient reported 75% clearing of her condition within 3 days of starting a treatment with a non-homogenous composition comprising ethanol (31%) and clobetasol (0.025%). The patient's chronic condition had failed to respond to oral antibiotics, topical antibiotics, topical cortisones including clobetasol cream. This treatment with a non-homogenous composition comprising ethanol (31%) and clobetasol (0.025%) worked when clobetasol cream under plastic (glove occlusion) and cortisone tape had failed.

Example 2-2

Treatment of Atopic Dermatitis (Eczema)

An 11 year old girl presented with recurrent persistent eczema only partly improved on the combined use of mometasone ointment and oral antibiotics. Within a week of starting a treatment with a non-homogenous composition comprising ethanol (31%) and mometasone (0.05%) the patient's condition was 85% clear.

Example 2-3

Treatment of Facial Eczema

Twenty-six patients with facial eczema were treated for two weeks twice daily with a non-homogenous ointment consisting of desonide 0.05% ointment mixed with 62% ethanol gel. The non-homogenous ointment was used in fixed ratios ranging from 10:1 to 1:1 (desonide ointment/ethanol gel), or as part of a progressive ratio therapy in which the initial ratio was 5:1 (desonide ointment/ethanol gel) and the ratio was changed every 2 days to 3:1, then 2:1 and ending at 1:1. Each preparation was prepared immediately prior to application. Results from all 26 patients are displayed in Table 2. Results from nine patients who used fixed ratios of desonide ointment/ethanol gel are displayed in Table 3. Results from 17 patients who underwent progressive ratio therapy are displayed in Table 4.

TABLE 2

Outcome of treatment using desonide/ethanol non-homogenous composition BID for 2 weeks in 26 patients with atopic dermatitis on the face:

| Outcome of Treatment | Number of patients with this outcome |
| --- | --- |
| worse | 0 |
| same | 1 |
| 25-50% better | 1 |
| 51-74% better | 1 |
| 75-99% better | 12 |
| 100% better | 11 |

TABLE 3

Outcome of treatment using fixed ratios of desonide/ ethanol non-homogenous composition BID for 2 weeks in 9 patients with atopic dermatitis on the face:

| | Number of patients with this outcome | | | |
| --- | --- | --- | --- | --- |
| Outcome of Treatment | 1:1 desonide/ EtOH | 4:1 desonide/ EtOH | 5:1 desonide/ EtOH | 10:1 desonide/ EtOH |
| worse | 0 | 0 | 0 | 0 |
| same | 0 | 0 | 0 | 0 |
| 25-50% better | 0 | 0 | 0 | 0 |
| 51-74% better | 0 | 0 | 0 | 0 |
| 75-99% better | 1 | 1 | 6 | 0 |
| 100% better | 0 | 0 | 0 | 1 |

TABLE 4

Outcome of treatment using progressive ratios of desonide/ ethanol non-homogenous composition BID for 2 weeks in 17 patients with atopic dermatitis on the face:

| Outcome of Treatment | Number of patients with this outcome |
| --- | --- |
| worse | 0 |
| same | 1 |
| 25-50% better | 1 |
| 51-74% better | 1 |
| 75-99% better | 4 |
| 100% better | 10 |

Based on the results from Table 2, the median improvement score was 87%. The mean improvement score was 86%. 88% of the patients achieved 75% or greater improvement compared to pretreatment. Treatment was well tolerated. None of the patients had to stop treatment due to irritation. Patients using compositions of different ratios of the desonide ointment and ethanol gel, ranging from 10:1 (desonide ointment/ ethanol gel) to 1:1, achieved comparable results in this study.

Example 2-4

Treatment of Atopic Dermatitis on the Trunk and/or Limbs

Forty-eight patients with trunk and/or limb eczema were treated for two weeks twice daily with a non-homogenous ointment consisting of mometasone furoate 0.1% ointment mixed with 62% ethanol gel. The non-homogenous ointment was used in fixed ratios ranging from 10:1 (mometasone furoate ointment/ethanol gel) to 1:1 or as part of a progressive ratio therapy in which the initial ratio was 5:1 mometasone ointment/ethanol gel and the ratio was changed every 2 days to 3:1, then 2:1 and ending at 1:1. Each preparation was prepared immediately prior to application. Results from all 48 patients are displayed in Table 5. Results from 13 patients who used fixed ratios of desonide ointment/ethanol gel are displayed in Table 6. Results from 35 patients who underwent progressive ratio therapy are displayed in Table 7.

TABLE 5

Outcome of treatment using mometasone/ethanol non-homogenous composition BID for 2 weeks in 48 patients with atopic dermatitis on the trunk and/or limbs:

| Outcome of Treatment | Number of patients with this outcome |
| --- | --- |
| worse | 0 |
| same | 1 |
| 25-50% better | 0 |
| 51-74% better | 0 |
| 75-99% better | 28 |
| 100% better | 19 |

TABLE 6

Outcome of treatment using fixed ratios of mometasone/ ethanol non-homogenous composition BID for 2 weeks in 13 patients with atopic dermatitis on the trunk and/or limbs:

| | Number of patients with this outcome | | | |
| --- | --- | --- | --- | --- |
| Outcome of Treatment | 1:1 mometasone/ EtOH | 4:1 mometasone/ EtOH | 5:1 mometasone/ EtOH | 10:1 mometasone/ EtOH |
| worse | 0 | 0 | 0 | 0 |
| same | 0 | 0 | 0 | 0 |
| 25-50% better | 0 | 0 | 0 | 0 |

TABLE 6-continued

Outcome of treatment using fixed ratios of mometasone/ethanol non-homogenous composition BID for 2 weeks in 13 patients with atopic dermatitis on the trunk and/or limbs:

| | Number of patients with this outcome | | | |
|---|---|---|---|---|
| Outcome of Treatment | 1:1 mometasone/ EtOH | 4:1 mometasone/ EtOH | 5:1 mometasone/ EtOH | 10:1 mometasone/ EtOH |
| 51-74% better | 0 | 0 | 0 | 0 |
| 75-99% better | 1 | 2 | 4 | 1 |
| 100% better | 0 | 1 | 4 | 0 |

TABLE 7

Outcome of treatment using progressive ratios of mometasone/ethanol non-homogenous composition BID for 2 weeks in 35 patients with atopic dermatitis on the trunk and/or limbs:

| Outcome of Treatment | Number of patients with this outcome |
|---|---|
| worse | 0 |
| same | 1 |
| 25-50% better | 0 |
| 51-74% better | 0 |
| 75-99% better | 20 |
| 100% better | 14 |

Based on the data from Table 5, the median improvement score was 87%. The mean improvement score was 90%. 98% of the patients achieved 75% or greater improvement compared to pretreatment. Treatment was well tolerated. None of the patients had to stop treatment due to irritation. Patients using compositions of different ratios of the mometasone ointment and ethanol gel, ranging from 10:1 (mometasone ointment/ethanol gel) to 1:1, achieved comparable results in this study.

Example 2-5

Summary of Corticosteroid-Ethanol Formulations Evaluated for the Treatment of Eczema Table 8 provides a summary of the corticosteroid formulations evaluated in the clinic for the treatment of eczema using the methods described herein. In all cases the eczema improved at least 75% compared to pretreatment, and the treatment was well-tolerated.

TABLE 8

| Structural Class of Corticosteroid | Corticosteroid tested | Ratio Corticosteroid Topical mixed with Ethanol gel | Concentration Ethanol gel |
|---|---|---|---|
| Class A Hydrocortisone Type | Hydrocortisone 2.5% ointment | 10:1 and 5:1 | 70% |
| | Hydrocortisone 1% OTC cream | 10:1 and 5:1 | 62% |
| Class B Triamcinalone Acetonide Type | Amcinonide 0.1% cream (Cyclocort ®) | 10:1 and 5:1 | 70% |
| | Amcinonide 0.1% ointment (Cyclocort ®) | 10:1 and 5:1 | 70% |
| | Desonide 0.05% cream | 4:1 and 1:1 | 62% |
| | Desonide 0.05% ointment | 10:1, 5:1, 4:1, 2:1, 1:1 | 62% |
| | Fluocinolone acetonide 0.025% ointment (Synalar ®) | 10:1 and 1:1 | 62% |
| | Fluocinonide 0.05% cream (Lidex ®) | 10:1 and 1:1 | 62% |
| | Fluocinonide 0.05% ointment (Lidex ®) | 10:1 and 1:1 | 62% |
| | Triamcinolone acetonide 0.1% cream | 1:1 | 62% |
| | Triamcinolone acetonide 0.1% ointment | 5:1 and 1:1 | 62% |
| | Triamcinalone diacetate 0.1% ointment | 10:1 and 5:1 | 62% |
| | Halocinonide 0.1% ointment (Halog ®) | 10:1 and 5:1 | 62% |
| | Halobetasol propionate 0.05% ung (Ultravate ®) | 10:1 and 5:1 | 62% |
| Class C Betamethasone Type | Clocortolone pivalate 0.1% cream (Cloderm ®) | 1:1 | 62% |
| | Desoximetasone 0.25% ointment | 10:1 and 5:1 | 70% |
| Class D1 Betamethasone Dipropionate Type | Alclometasone dipropionate 0.05% (Aclovate ®) Ointment | 10:1 and 5:1 | 70% |
| | Betamethasone dipropionate 0.05% ointment (Diprolene ®) | 10:1 and 5:1 | 70% |
| | Betamethasone dipropionate augmented 0.05% ointment | 10:1 and 5:1 | 62% |
| | Betamethasone valerate 0.1% ointment | 10:1 and 5:1 | 62% |
| | Fluticasone propionate 0.005% cream (Cutivate ®) | 10:1 and 5:1 | 62% |
| | Fluticasone propionate 0.005% ointment (Cutivate ®) | 10:1 and 5:1 | 62% |
| | Mometasone 0.1% ointment | 10:1, 5:1, 4:1, 2:1, 1:1 | 62% |
| | Diflorasone diacetate 0.05% ointment (Psorcon ®) | 10:1 and 5:1 | 70% |
| | Clobetasol propionate 0.05% ointment (Temovate ®) | 4:1 and 1:1 | 62% |
| | Clobetasol propionate 0.05% cream (Temovate ®) | 5:1 | 62% |
| Class D2 Methyl-prednisolone Aceponate | Hydrocortisone Butyrate 0.1% ointment (Locoid ®) | 10:1 and 5:1 | 62% |

TABLE 8-continued

| Structural Class of Corticosteroid | Corticosteroid tested | Ratio Corticosteroid Topical mixed with Ethanol gel | Concentration Ethanol gel |
|---|---|---|---|
| Type | Hydrocortisone Butyrate 0.1% cream (Locoid ®) | 10:1 | 62% |
| | Hydrocortisone valerate 0.2% ointment | 10:1 and 5:1 | 70% |
| | Prednicarbate 0.1% cream | 10:1 and 5:1 | 62% |
| Uncertain structural class | fluradrenolide 0.05% cream (potency class 5) | 10:1 and 5:1 | 62% |

Example 2-6

Summary of Outcomes of Various Combinations of Topical Corticosteroids and Ethanol for Treating Eczema (Arranged Alphabetically)

Table 9 provides a summary of outcomes using the methods described herein of various combinations of topical corticosteroids and ethanol. In all cases the treatment was well-tolerated.

TABLE 9

| Topical CS tested | Initial CS concentration present in topical preparation | Ratio by volume of topical CS and 62% ethanol gel in the mixture* | Amount of reduction in CS concentration in final mixture | Net CS concentration in the non-homogenous mixture as administered | Number of patients treated | % patients achieving treatment success** |
|---|---|---|---|---|---|---|
| Alclometasone dipropionate Ung (Aclovate ®) | 0.050% | 5:1 | 1/6 | 0.042% | 1 | 100% |
| Amcinonide Cr (Cyclocort ®) | 0.100% | 5:1 | 1/6 | 0.083% | 1 | 100% |
| Amcinonide Ung (Cyclocort ®) | 0.100% | 5:1 | 1/6 | 0.083% | 1 | 100% |
| Betamethasone propionate Aug Ung (Diprolene ®) | 0.050% | 5:1 | 1/6 | 0.042% | 1 | 100% |
| Betamethasone propionate Ung (Diprolene ®) | 0.050% | 5:1 | 1/6 | 0.042% | 1 | 100% |
| Betamethasone valerate Ung (Valisone ®) | 0.100% | 5:1 | 1/6 | 0.083% | 1 | 100% |
| Clobetasol propionate Cr (Temovate ®) | 0.050% | 5:1 | 1/6 | 0.042% | 1 | 100% |
| Clobetasol propionate Ung (Temovate ®) | 0.050% | 1:1 | 1/2 | 0.025% | 2 | 100% |
| Clobetasol propionate Ung (Temovate ®) | 0.050% | 4:1 | 1/5 | 0.040% | 1 | 100% |
| Clocortolone pivalate Cr (Cloderm ®) | 0.100% | 1:1 | 1/2 | 0.050% | 1 | 100% |
| Desonide Cr | 0.050% | 4:1 | 1/5 | 0.040% | 1 | 100% |
| Desonide Cr | 0.050% | 2:1 | 1/3 | 0.033% | 1 | 100% |
| Desonide Cr | 0.050% | 1:1 | 1/2 | 0.025% | 2 | 100% |
| Desonide Ung | 0.050% | 1:1 | 1/2 | 0.025% | 28 | 96% |
| Desonide Ung | 0.050% | 10:1 | 1/11 | 0.046% | 6 | 100% |
| Desonide Ung | 0.050% | 2:1 | 1/3 | 0.033% | 2 | 100% |
| Desonide Ung | 0.050% | 4:1 | 1/5 | 0.040% | 2 | 100% |
| Desonide Ung | 0.050% | 5:1 | 1/6 | 0.042% | 18 | 94% |
| Desoximetasone Ung (Topicort ®) | 0.250% | 5:1 | 1/6 | 0.21% | 3 | 100% |
| Diflorasone diacetate Ung (Psorcon ®) | 0.050% | 5:1 | 1/6 | 0.042% | 1 | 100% |
| Fluocinolone acetonide Ung (Synalar ®) | 0.025% | 5:1 | 1/6 | 0.021% | 2 | 100% |

TABLE 9-continued

| Topical CS tested | Initial CS concentration present in topical preparation | Ratio by volume of topical CS and 62% ethanol gel in the mixture* | Amount of reduction in CS concentration in final mixture | Net CS concentration in the non-homogenous mixture as administered | Number of patients treated | % patients achieving treatment success** |
|---|---|---|---|---|---|---|
| Fluocinonide Cr (Lidex ®) | 0.050% | 1:1 | ½ | 0.025% | 4 | 100% |
| Fluocinonide Ung (Lidex ®) | 0.050% | 1:1 | ½ | 0.025% | 2 | 100% |
| Flurandrenolide Cr (Cordran SP ®) | 0.050% | 5:1 | ⅙ | 0.042% | 2 | 100% |
| Fluticasone propionate Ung (Cutivate ®) | 0.005% | 5:1 | ⅙ | 0.004% | 3 | 100% |
| Halobetasol propionate Cr (Ultravate ®) | 0.050% | 5:1 | ⅙ | 0.042% | 1 | 100% |
| Halocinonide Cr (Halog ®) | 0.100% | 1:1 | ½ | 0.050% | 1 | 100% |
| Hydrocortisone Cr OTC | 1.000% | 5:1 | ⅙ | 0.833% | 1 | 100% |
| Hydrocortisone Ung | 2.5% | 5:1 | ⅙ | 2.083% | 1 | 100% |
| Hydrocortisone butyrate Cr (Locoid ®) | 0.100% | 5:1 | ⅙ | 0.083% | 1 | 100% |
| Hydrocortisone butyrate Ung (Locoid ®) | 0.100% | 5:1 | ⅙ | 0.083% | 2 | 100% |
| Hydrocortisone valerate Ung (Westcort ®) | 0.200% | 5:1 | ⅙ | 0.167% | 1 | 100% |
| Mometasone Cr (Elocon ®) | 0.100% | 1:1 | ½ | 0.050% | 2 | 100% |
| Mometasone Cr (Elocon ®) | 0.100% | 2:1 | ⅓ | 0.067% | 1 | 100% |
| Mometasone Cr (Elocon ®) | 0.100% | 5:1 | ⅙ | 0.083% | 1 | 100% |
| Mometasone Ung (Elocon ®) | 0.100% | 5:1 | ⅙ | 0.083% | 14 | 93% |
| Mometasone Ung (Elocon ®) | 0.100% | 1:1 | ½ | 0.050% | 27 | 96% |
| Mometasone Ung (Elocon ®) | 0.100% | 10:1 | 1/11 | 0.091% | 5 | 77% |
| Mometasone Ung (Elocon ®) | 0.100% | 2:1 | ⅓ | 0.067% | 5 | 100% |
| Mometasone Ung (Elocon ®) | 0.100% | 4:1 | ⅕ | 0.080% | 6 | 100% |
| Mometasone Ung (Elocon ®) | 0.100% | 3:1 | ¼ | 0.075% | 2 | 100% |
| Prednicarbate Ung (Dermatop ®) | 0.100% | 5:1 | ⅙ | 0.083% | 1 | 100% |
| Triamcinolone acetonide Cr (Kenalog ®) | 0.100% | 1:1 | ½ | 0.050% | 1 | 100% |
| Triamcinolone acetonide Ung (Kenalog ®) | 0.100% | 1:1 | ½ | 0.050% | 1 | 100% |
| Triamcinolone acetonide Ung (Kenalog ®) | 0.100% | 5:1 | ⅙ | 0.083% | 2 | 100% |
| Triamcinolone diacetate Ung (Aristocort ®) | 0.100% | 5:1 | ⅙ | 0.083% | 1 | 100% |

CS = corticosteroid

*The ratio is the relative amount of the topical corticosteroid to be combined with the ethanol gel to form the mixture. For example: 5 to 1 ratio means 5 parts corticosteroid to 1 part ethanol gel. This results in a final corticosteroid concentration which is ⅚ of the initial concentration or a 17% drop in initial corticosteroid concentration.

**Success is defined as 75% or greater reduction in amount of eczema rash compared to pretreatment.

Example 2-7

Comparison of the Results of Clinical Trials for Treating Eczema in Children with Corticosteroid/Ethanol Non-Homogenous Composition Versus Published Results for Using Conventional Treatment 1) Topical Mometasone/Ethanol Prototype Compared to "Bleach Baths" in Treating Children with Eczema.

A recent study (Huang J T, Abrams M, Tlougan B, Rademaker A, Paller A S. Treatment of staphylococcus aureus colonization in atopic dermatitis decreases disease severity. *Pediatrics May* 2009; 123(5): 808-814) evaluated a new method for treating eczema employing "bleach baths" to topical corticosteroid treatment as a means to suppress the staphylococcal population on the skin. This bleach bath-topical corticosteroid treatment resulted in a mean improvement of 40% in 1 month of use. These results were inferior to twice daily treatment of prototype non-homogenous ointment consisting of mometasone furoate 0.1% ointment mixed with 62% ethanol gel in fixed or progressive ratios, which resulted in a mean improvement of 90% in two weeks (data presented in Table 5).

2) Topical Desonide/Ethanol Non-Homogenous Composition Compared to Conventional Desonide Formulations in Treating Children with Eczema.

The use of commercially available desonide formulations in treating children with eczema has been reported in the literature. Desonide 0.05% hydrogel and desonide 0.05% ointment provided 25% and 34% success, respectively, after 2 weeks of therapy and 25% and 52% success, respectively, after 3-6 weeks of therapy (Trookman N S, Rizer R L. Randomized Controlled Trial of Desonide Hydrogel 0.05% versus Desonide Ointment 0.05% in the Treatment of Mild-to-moderate Atopic Dermatitis. *J Clin Aesthet Dermatol.* November 2011; 4(11): 34-38). Another study showed that desonide 0.05% hydrogel and its hydrogel vehicle provided 19% and 3% success, respectively, after 2 weeks of therapy and 39% and 11% success, respectively, after 3-6 weeks of therapy (Hebert A A, Cook-Bolden F E, Basu S, Calvarese B, Trancik R J. Safety and efficacy of desonide hydrogel 0.05% in pediatric subjects with atopic dermatitis. *J Drugs Dermatol.* February 2007; 6(2):175-81). In these two studies, the desonide hydrogel contains propylene glycol in its vehicle and the desonide ointment contains no alcohol. In sharp contrast, prototype non-homogenous ointment consisting of a mixture of desonide/ethanol in fixed or progressive ratios led to 88% success after two weeks of twice daily treatment (data shown in Table 2). The prototype non-homogenous ointment provided better results in a shorter period of time. In all studies, success was defined as the percentage of patients that achieved 75% or better improvement compared to baseline.

3) Topical Mometasone/Ethanol Non-Homogenous Composition Compared to Conventional Mometasone Cream in Treating Children with Eczema.

The use of commercially available mometasone formulations for the treatment of children with eczema has been reported in the literature. One study found that mometasone 0.1% cream provided 50% success after 3 weeks of therapy (Rafanelli A, Rafanelli S, Stanganelli I, et. al. Mometasone furoate in the treatment of atopic dermatitis in children. *J. Eur. Acad. Dermatol. Venereol.* 1993; 2(3):225-230). Another study found that mometasone 0.1% cream led to 63% success after 3 weeks of therapy (Vernon H J, Lane A T, Weston W. Comparison of mometasone furoate 0.1% cream and hydrocortisone 1.0% cream in the treatment of childhood atopic dermatitis. *J. Am. Acad. Dermatol. April* 1991; 24:603-7). A third study reported overall results similar to the other two studies (Lebwohl M, Lane A T, Berman B, et. al. Efficacy and safety of 0.1% mometasone furoate cream versus 0.2% hydrocortisone valerate cream in pediatric patients with atopic dermatitis un-responsive to topical hydrocortisone treatment. Proceedings of the 55th Annual Meeting of the American Academy of Dermatology Mar. 21-26, 1997; abstract number P-43). In all cases, the mometasone 0.1% cream included propylene glycol stearate (55% monoester) in its vehicle. Use of the prototype non-homogenous ointment consisting of a mixture of mometasone/ethanol in fixed or progressive ratios provided 98% success after only two weeks of twice daily treatment (data in Table 5). In all studies, success was defined as percentage of patients achieving 75% or better improvement compared to baseline.

Example 2-8

Clinical Trial of Moisturizer/Ethanol Non-Homogenous Composition in Preventing Recurrence of Eczema Demographics: 7 patients with chronic recurrent eczema entered the trial. Prior to starting the trial all had cleared their eczema rash using rash treatment prototype topical therapy. All had a past history of conventional moisturizers failing to prevent recurrence of eczema within 10 days of stopping prior rash therapy.

Protocol: All used maintenance non-homogenous lotion twice a day.

Materials: The maintenance non-homogenous lotion was Cetaphil™ moisturizing lotion mixed in a ratio of 1:1 with 62% ethanol gel immediately before application.

Duration of follow-up:
a. 1 month: 2 patients
b. 1.5 months: 1 patient
c. 2 months: 2 patients
d. 6 months: 1 patient
e. 7 months: 1 patient Outcome of Protocol Treatment: 6 of the 7 patients reported they stayed entirely clear while on consistent use maintenance therapy. One patient reported when the weather got very cold and dry, the rash recurred despite the maintenance therapy.

Conclusion

The maintenance prototype was strikingly effective in maintaining patients rash-free.

Example 2-9

Two Case Studies Demonstrating Killing or Inhibition of *S. aureus* Growth Using Corticosteroid/Ethanol Non-Homogenous Compositions Case 1: A 26-year old man with eczema on the hand was treated twice daily for three days with a mixture of triamcinolone 0.1% ointment in a 5:1 ratio with 62% ethanol gel. The pre-treatment bacterial culture from the eczematous rash reported growth of *S. aureus*. The post-treatment bacterial culture performed after three days of treatment showed no *S. aureus* present.

Case 2: A 92-year old man with eczema on the hand was treated twice daily for seven days with a mixture of fluocinolone 0.1% ointment in a 1:1 ratio with 62% ethanol gel. The pre-treatment bacterial culture from the eczematous rash reported growth of *S. aureus*. The post-treatment bacterial culture performed after seven days of treatment showed no *S. aureus* present.

Example 2-10

Non-Stinging Test Using Superficial Skin Abrasion Model

In a study with 20 subjects, this test is performed on a total of 6 sites on each subject: three test sites on each arm. Tape is used to sequentially strip the skin until the glistening layer is visible. The test materials include a positive stinging control (70% ethanol solution), a negative stinging control (formulation vehicle without ethanol) and the novel formulation with ethanol (with or without a second active agent). Each material is applied to a single site on each forearm to allow for a separate determination of response consistency. Each material is applied for 15 seconds to each site. Each subject reports the intensity of the stinging/burning sensation on a 0-4 point scale. The outcome of the study is determined by comparing the scores of all the sites.

Example 2-11

Treatment of Tinea Versicolor

Tinea versicolor is a rash in humans known to be caused by two species of malassezia: malassezia globosa and malassezia furfur.

The patient was a 39 year old man with a two-year history of extensive tan moderately scaling patches symmetrically on the chest and back. Condition failed to respond to a month of conventional treatment with zinc pyrithione lotion. The diagnosis was confirmed by a KOH microscopic examination of a specimen from the back rash showing very large numbers of short fat hyphae and round yeasts.

Treatment of once daily application of 70% ethanol gel to affected areas for two weeks was begun. The patient reported that the treatment was well tolerated and comfortable to perform.

The course of treatment resulted in the back patches post-treatment showing 10% of the pretreatment scaling. KOH microscopic examination of the rash done post treatment showed complete absence of hyphae and round yeast. The chest patches post treatment had 25% of pretreatment scaling. The KOH microscopic examination of the specimen post treatment showed rare short fat hyphae and no round yeasts.

Conclusions: Ethanol killed malassezia genus organisms in this in vivo therapeutic trial. The patient demonstrated improvement in the rash both as measured by clinical examination and microscopic assessment.

Example 2-12

Treatment of Seborrheic Dermatitis

The patient was a 79-year old man with a prolonged, multi-year history of facial seborrheic dermatitis which failed to respond adequately to either a low potency prescription corticosteroid cream (hydrocortisone valerate 0.2%), or to a mid-potency corticosteroid cream (mometasone 0.1%) in combination with an anti-fungal cream (ketoconazole cream). In a trial of the compositions described herein, he applied twice a day for 6 days a non-homogenous 10:1 mixture of hydrocortisone butyrate cream 0.1% (10 parts) and 62% ethanol gel (1 part). This course of therapy resulted in 100% clearing of the facial areas treated and was well tolerated. The patient reported he had never cleared this much, or this fast, from any of the prior therapies.

Example 2-13

Treatment of Persistent Eczema

A chemical matrix for the treatment of eczema using triamcinalone acetonide and ethanol was prepared as described in Example 1-3 using the following ingredients:
2.5 ml of triamcinalone acetonide cream 0.1%;
2.5 ml of Aquaphore; and
1 ml of 62% ethanol gel.
The final concentration of active ingredients in this new chemical matrix are: triamcinalone acetonide 0.042%, and ethanol 10.3%.

A 64-year-old woman presented with extensive, extremely itchy, crusted eczema on the trunk and legs and such a condition had existed for over a year. The condition persisted despite treatment with triamcinalone acetonide cream 0.1% used daily for more than 9 months. No improvement was observed when she covered the areas treated with the triamcinalone cream for 8 hours with wet pajamas. Treatment was begun using the same triamcinalone acetonide 0.1% cream but now reformulated into the chemical matrix described above. The triamcinalone acetonide and ethanol matrix was applied twice daily without any wet covering. The patient reported within 24 hours of treatment the itching was greatly reduced. When examined after 1 week of treatment, the former rash was 95% resolved.

Example 2-14

Treatment of Persistent Pediatric Eczema

A chemical matrix for the treatment of eczema using desonide and ethanol was prepared as described in Example 1-3 using the following ingredients:
2.5 ml of desonide ointment 0.05%;
2.5 ml of Aquaphore; and
1 ml of 62% ethanol gel.
The final concentration of active ingredients in this new chemical matrix are: desonide 0.021%, and ethanol 10.3%.

An 18-month-old child presented with extensive, extremely itchy, crusted eczema on the face, trunk, arms, and legs persisting for several months, worsening in the preceding 10 days. Treatment with moisturizing creams and 1% hydrocortisone cream did not resolve the rash. Treatment was begun using the desonide and ethanol matrix described above. The desonide and ethanol matrix was applied twice daily. The parents reported the rash was almost entirely resolved at 4 days of treatment.

While preferred embodiments of the present inventions have been shown and described herein, it will be obvious to those skilled in the art that such embodiments are provided by way of example only. Numerous variations, changes, and substitutions will now occur to those skilled in the art without departing from the inventions. It should be understood that various alternatives to the embodiments of the invention described herein may be employed in practicing the invention. It is intended that the following claims define the scope of the inventions and that methods and structures within the scope of these claims and their equivalents be covered thereby.

What is claimed is:

1. A chemical matrix comprising from about 2% to about 30% of an alcohol by volume, a corticosteroid and at least one excipient, wherein the chemical matrix is an ointment suitable for topical non-systemic administration, the alcohol is primarily dispersed into the chemical matrix in the form of microbubbles, and the alcohol is selected from ethanol, isopropanol, or n-propanol.

2. The chemical matrix of claim 1, wherein the alcohol is ethanol.

3. The chemical matrix of claim 1, wherein the ointment is selected from white petrolatum USP, white ointment USP, hydrophilic petrolatum USP, or hydrophilic ointment USP.

4. The chemical matrix of claim 1, wherein the corticosteroid is selected from desonide, or mometasone.

5. The chemical matrix of claim 2, wherein the chemical matrix comprises from about 2% to about 10% ethanol by volume.

6. The chemical matrix of claim 2, wherein the chemical matrix comprises from about 10% to about 20% ethanol by volume.

7. The chemical matrix of claim 2, wherein the chemical matrix comprises from about 20% to about 30% ethanol by volume.

8. The chemical matrix of claim 5, wherein the corticosteroid is selected from desonide, or mometasone.

9. The chemical matrix of claim 6, wherein the corticosteroid is selected from desonide, or mometasone.

10. The chemical matrix of claim 7, wherein the corticosteroid is selected from desonide, or mometasone.

11. The chemical matrix of claim 4, wherein the corticosteroid comprises from about 0.1% (w/w) to about 0.0001% (w/w) of the chemical matrix.

12. The chemical matrix of claim 8, wherein the corticosteroid comprises from about 0.1% (w/w) to about 0.0001% (w/w) of the chemical matrix.

13. The chemical matrix of claim 9, wherein the corticosteroid comprises from about 0.1% (w/w) to about 0.0001% (w/w) of the chemical matrix.

14. The chemical matrix of claim 10, wherein the corticosteroid comprises from about 0.1% (w/w) to about 0.0001% (w/w) of the chemical matrix.

15. A method of treating a skin disease or disorder in an individual in need thereof comprising topical application to the individual of a chemical matrix comprising from about 2% to about 30% of an alcohol by volume, a corticosteroid and at least one excipient, wherein the chemical matrix is an ointment suitable for topical non-systemic administration, the alcohol is primarily dispersed into the chemical matrix in the form of microbubbles, and the alcohol is selected from ethanol, isopropanol, or n-propanol.

16. The method of claim 15, wherein the alcohol is ethanol.

17. The method of claim 15, wherein the ointment is selected from white petrolatum USP, white ointment USP, hydrophilic petrolatum USP, or hydrophilic ointment USP.

18. The method of claim 15, wherein the corticosteroid is selected from desonide, or mometasone.

19. The method of claim 16, wherein the chemical matrix comprises from about 2% to about 10% ethanol by volume.

20. The method of claim 16, wherein the chemical matrix comprises from about 10% to about 20% ethanol by volume.

21. The method of claim 16, wherein the chemical matrix comprises from about 20% to about 30% ethanol by volume.

22. The method of claim 19, wherein the corticosteroid is selected from desonide, or mometasone.

23. The method of claim 20, wherein the corticosteroid is selected from desonide, or mometasone.

24. The method of claim 21, wherein the corticosteroid is selected from desonide, or mometasone.

25. The method of claim 15, wherein the skin disease or disorder is dermatitis.

26. The method of claim 15, wherein the skin disease or disorder is eczema.

27. The method of claim 15, wherein the skin disease or disorder is atopic dermatitis.

* * * * *